US012622867B2

(12) United States Patent
Sontum et al.

(10) Patent No.: US 12,622,867 B2
(45) Date of Patent: May 12, 2026

(54) TREATMENT OF PANCREATIC CANCER

(71) Applicant: EXACT THERAPEUTICS AS, Oslo (NO)

(72) Inventors: Per Christian Sontum, Oslo (NO); Andrew John Healey, Moss (NO); Svein Kvale, As (NO)

(73) Assignee: EXACT THERAPEUTICS AS, Oslo (NO)

( * ) Notice: Subject to any disclaimer, the term of this patent is extended or adjusted under 35 U.S.C. 154(b) by 1053 days.

(21) Appl. No.: 17/755,221

(22) PCT Filed: Oct. 23, 2020

(86) PCT No.: PCT/NO2020/050260
§ 371 (c)(1),
(2) Date: Apr. 22, 2022

(87) PCT Pub. No.: WO2021/080438
PCT Pub. Date: Apr. 29, 2021

(65) Prior Publication Data
US 2022/0378692 A1 Dec. 1, 2022

(30) Foreign Application Priority Data

Oct. 25, 2019 (NO) .................................. 20191277

(51) Int. Cl.
| | |
|---|---|
| A61K 9/00 | (2006.01) |
| A61K 9/107 | (2006.01) |
| A61K 9/50 | (2006.01) |
| A61K 31/337 | (2006.01) |
| A61K 31/4745 | (2006.01) |
| A61K 45/06 | (2006.01) |
| A61P 35/00 | (2006.01) |

(52) U.S. Cl.
CPC .......... *A61K 9/0009* (2013.01); *A61K 9/1075* (2013.01); *A61K 9/5015* (2013.01); *A61K 31/337* (2013.01); *A61K 31/4745* (2013.01); *A61K 45/06* (2013.01); *A61P 35/00* (2018.01)

(58) Field of Classification Search
CPC .. A61K 9/0009; A61K 9/1075; A61K 9/5015; A61K 31/337; A61K 31/4745; A61K 45/06; A61K 31/7068; A61P 35/00; A61N 2007/0039; A61N 2007/0073; A61N 7/00
See application file for complete search history.

(56) References Cited

U.S. PATENT DOCUMENTS

| | | |
|---|---|---|
| 6,165,440 A | 12/2000 | Esenaliev |
| 8,345,821 B2 | 1/2013 | Sumanaweera et al. |
| 9,629,610 B2 | 4/2017 | Sandstrom et al. |
| 12,343,396 B2 | 7/2025 | Healey et al. |
| 12,377,146 B2 | 8/2025 | Healey et al. |
| 2003/0204141 A1 | 10/2003 | Nock et al. |
| 2004/0081623 A1 | 4/2004 | Eriksen et al. |
| 2006/0025756 A1 | 2/2006 | Francischelli et al. |
| 2007/0178047 A1 | 8/2007 | Kawabata |
| 2008/0242979 A1 | 10/2008 | Fisher et al. |
| 2008/0299084 A1 | 12/2008 | Brahmbhatt et al. |
| 2009/0252773 A1 | 10/2009 | Yoneda et al. |
| 2010/0298709 A1 | 11/2010 | Needles et al. |
| 2012/0165665 A1 | 6/2012 | Sandstrom et al. |
| 2013/0131495 A1 | 5/2013 | Konofagou et al. |
| 2013/0289398 A1 | 10/2013 | Borden et al. |
| 2015/0258353 A1 | 9/2015 | Partanen et al. |
| 2015/0273061 A1 | 10/2015 | Trogler et al. |
| 2016/0243234 A1 | 8/2016 | Healey |
| 2018/0200196 A1 | 7/2018 | Fahmy et al. |
| 2019/0216478 A1 | 7/2019 | Maxwell et al. |
| 2020/0254285 A1 | 8/2020 | Jang et al. |
| 2020/0306564 A1 | 10/2020 | Bar-Zion et al. |
| 2020/0323515 A1 | 10/2020 | Levy |
| 2020/0405258 A1 | 12/2020 | Dayton et al. |
| 2021/0299256 A1 | 9/2021 | Healey |
| 2022/0305139 A1 | 9/2022 | Kim et al. |
| 2023/0211020 A1 | 7/2023 | Kvåle et al. |
| 2023/0218759 A1 | 7/2023 | Healey et al. |
| 2023/0218760 A1 | 7/2023 | Healey et al. |
| 2023/0233681 A1 | 7/2023 | Healey et al. |
| 2023/0241216 A1 | 8/2023 | Healey et al. |

(Continued)

FOREIGN PATENT DOCUMENTS

| | | |
|---|---|---|
| CN | 108815725 A | 11/2018 |
| EP | 0727225 A3 | 1/1997 |

(Continued)

OTHER PUBLICATIONS

Kotopoulis et al., "Sonoporation with Acoustic Cluster Therapy (ACT®) Induces Transient Tumour Volume Reduction in a Subcutaneous Xenograft Model of Pancreatic Ductal Adenocarcinoma," Journal of Controlled Release, 2017, pp. 70-80, vol. 245, http://dx.doi.org/10.1016/j.jconrel.2016.11.019, in 11 pages.

(Continued)

*Primary Examiner* — Robert S Cabral

(74) *Attorney, Agent, or Firm* — Knobbe, Martens, Olson & Bear LLP

(57) ABSTRACT

The present invention relates to ultrasound mediated delivery of therapeutic agents to the pancreas, and particularly for treatment of pancreatic cancer such as pancreatic ductal adenocarcinoma (PDAC). More particularly, the invention provides a cluster composition and a pharmaceutical composition, for use in delivery of therapeutic agents and for treatment of pancreatic cancers, including PDAC.

9 Claims, 9 Drawing Sheets

(56)                     References Cited

U.S. PATENT DOCUMENTS

2024/0216549 A1    7/2024   Sontum et al.
2024/0269489 A1    8/2024   Kvåle et al.
2024/0358984 A1   10/2024   Kvåle et al.
2024/0359037 A1   10/2024   Sontum et al.
2025/0235536 A1    7/2025   Kvåle et al.
2025/0272845 A1    8/2025   Healey et al.

FOREIGN PATENT DOCUMENTS

EP           1842560          10/2007
EP           2468191 A1        6/2012
EP           2521593 B1       11/2012
EP           3901172 A1       10/2021
EP           4008358 A1        6/2022
EP           4048231 A1        8/2022
GB           2595513 A        12/2021
JP           2005168312        6/2005
JP           2007197403        8/2007
JP           2008526785        7/2008
JP           2016-532718 A    10/2016
WO      WO 1994/016379 A1      7/1994
WO           96/39197 A1      12/1996
WO           98/01732 A1       1/1998
WO      WO 98/17324            4/1998
WO      WO 1998/051284 A1     11/1998
WO      WO 99/39738            8/1999
WO      WO 99/53693           10/1999
WO      WO 99/53963           10/1999
WO      WO 99/53965           10/1999
WO      WO 1999/053963 A1     10/1999
WO      WO 2005/063306         7/2005
WO      WO 2015/047103         4/2015
WO      WO 2015/047103 A1      4/2015
WO      WO 2017/080481         5/2017
WO      WO 2018/126322         7/2018
WO      WO 2019/094802         5/2019
WO      WO 2020/115491         6/2020
WO      WO 2021/045485         3/2021
WO           2021/069971 A1    4/2021
WO      WO 2021/080438         4/2021
WO      WO 2021/118783         6/2021
WO           2021/150446 A1    7/2021
WO      WO 2021/224921        11/2021
WO           2021/239878 A1   12/2021
WO      WO 2022/069377         4/2022

OTHER PUBLICATIONS

Sontum et al., "Acoustic Cluster Therapy—A Novel Approach for Ultrasound Mediated Targeted Drug Delivery: Technology Basics and Proof of Concept," 2016, Department of Physics, NTNU, Trondheim, Norway, Phoenix Solutions AS, Oslo, Norway, Joint Department of Physics, ICR, London, U.K., in 4 pages.
Van Wamel et al., "Acoustic Cluster Therapy (ACT): A Novel Concept for Targeted Drug Delivery—In Vivo Characteristics and Proof of Principle," Conference Paper, Jan. 2015, https://www.researchgate.net/publication/277583076, in 5 pages.
Van Wamel et al., "Acoustic Cluster Therapy (ACT)—Pre-Clinical Proof of Principle for Local Drug Delivery and Enhanced Uptake," Journal of Controlled Release, Feb. 28, 2016, pp. 158-164, vol. 224, https://doi.org/10.1016/j.jconrel.2016.01.023, in 7 pages.
International Search Report and Written Opinion of PCT/NO2014/050177, Dated Jan. 15, 2015, in 11 pages.
International Search Report and Written Opinion of PCT/NO2020/050260 dated Feb. 11, 2021 in 10 pages.
Åslund, Andreas K.O. et al "Efficient Enhancement of Blood-Brain Barrier Permeability Using Acoustic Cluster Therapy (ACT)", Theranostics 2017, vol. 7, Issue 1, doi: 10.7150/thno.16577.
Dimcevski, Georg et al "A human clinical trial using ultrasound and microbubbles to enhance gemcitabine treatment of inoperable pancreatic cancer", Journal of Controlled Release, 2016, vol. 243, pp. 172-181, http://dx.doi.org/10.1016/j.jconrel.2016.10.007.

Kotopoulis, Spiros et al "Sonoporation with Acoustic Cluster Therapy (ACT®) induces transient tumour vol. reduction in a subcutaneous xenograft model of pancreatic ductaladenocarcinoma", Journal of Controlled Release, Nov. 18, 2016, vol. 245, pp. 70-80, ISSN 0168-3659, Elsevier, doi:10.1016/j.jconrel.2016.11.019.
Miller et al., "Bioeffects Considerations for Diagnostic Ultrasound Contrast Agents", Journal of Ultrasound Med 2008; vol. 27, pp. 611-632.
Nigel Bush et al "Acoustic Cluster Therapy displays theranostic capability in enhancing the effectiveness of liposomal doxorubicin treatment of human triple negative breast cancer in mice", 2019 IEEE International Ultrasonics Symposium (IUS), Glasgow, Scotland, Oct. 6-9, 2019.
Postema et al., "Contrast-enhanced and Targeted Untrasound", World Journal of Gastroenterol, Jan. 7, 2022, vol. 17, pp. 28-41.
Schultz Christopher W et al: Selecting the Optimal Parameters for Sonoporation of Pancreatic Cancer in a Pre-Clinical Model 2019 IEEE International Ultrasonics Symposium (IUS), IEEE, Oct. 6, 2019 (Oct. 6, 2019), pp. 328-331, XP033671248, DOI: 10.1109/ULTSYM.2019.8925889.
Van Wamel, Annemieke et al "Acoustic Cluster Therapy (ACT) enhances the therapeutic efficacy of paclitaxel and Abraxane® for treatment of human prostate adenocarcinoma in mice", Journal of Controlled Release, 2016, vol. 236, pp. 15-21, ISSN 0168-3659, doi:10.1016/j.jconrel.2016.06.018.
Andersen et al., "A harmonic dual-frequency transducer for acoustic cluster therapy." Ultrasound Med Biol. Sep. 1, 2019;45(9):2381-2390.
Aoki et al., "Image of tumor matastasis and inflammatory lymph node enlargement by contrast-enhanced ultrasonography," Word Journal of Radiology, Dec. 28, 2011, pp. 298-305.
Argenziano et al., Vancomycin-loaded nanobubbles: A new platform for controlled antibiotic delivery against methicillin-resistant Staphylococcus aureus infections. Int'l J Pharma. May 15, 2017;523(1):176-188.
Beccaria et al., "Ultrasound-induced opening of the blood-brain barrier to enhance temozolomide and irinotecan delivery: an experimental study in rabbits," Journal of Neurosurgery, vol. 124, No. 6, Jun. 1, 2016, pp. 1602-1610.
Brighi, "MR-guided focused ultrasound increases antibody delivery to nonenhancing high-grade glioma," Neuro-Oncology Advances, vol. 2, No. 1, Mar. 5, 2020 in 12 pages.
Bulner et al., "Enhancing Checkpoint Inhibitor Therapy with Ultrasound Stimulated Microbubbles," Ultrasound in Medicine and Biology, vol. 45, No. 2, Nov. 15, 2018, pp. 500-512.
Bush et al., "Acoustic Cluster Therapy displays theranostic capability in enhancing the effectiveness of liposomal doxorubicin treatment of human triple negative breast cancer in mice," In 2019 IEEE International Ultrasonics Symposium, Oct. 6, 2019, pp. 224-226.
Bush et al., "Ultrasound, optical and photoacoustic imaging of Acoustic Cluster Therapy enhanced delivery to human tumors in mice," In 2019 IEEE International Ultrasonics Symposium [IUS], Oct. 6, 2019, pp. 1556-1559.
Bush et al., "Therapeutic Dose Response of Acoustic Cluster Therapy in Combination With Irinotecanfor the Treatment of Human Colon Cancer in Mice," Front Pharmacol. Nov. 19, 2019;10:1299 in 14 pages.
Bush et al., "Theranostic Attributes of Acoustic Cluster Therapy and Its Use for Enhancing the Effectiveness of Liposomal Doxorubicin Treatment of Human Triple Negative Breast Cancer in Mice," Front Pharmacol. Feb. 20, 2020;11:75 in 11 pages.
Carpentier et al., "Clinical trial of blood-brain barrier disruption by pulsed ultrasound," Science Translational Medicine, vol. 8, No. 343, Jun. 15, 2016 in 8 pages.
Carter et al., "Immune-oncology agents for cancer therapy." Pharm. J. May 2020;304(7937): S2-S27.
Castle et al., "Ultrasound-mediated targeted drug delivery: recent success and remaining challenges". Am J Physiol Heart Circ Physiol. Feb. 2013;304(3):H350-7.
Chen et al., "Focused ultrasound-induced blood-brain barrier opening to enhance interleukin-12 delivery for brain tumor immunotherapy:

(56) References Cited

OTHER PUBLICATIONS a preclinical feasibility study," Journal of Translational Medicine, vol. 13, No. 1, Mar. 17, 2015 in 12 pages.

Chen et al., "Theranostic Strategy of Focused Ultrasound Induced Blood-Brain Barrier Opening for CNS Disease Treatment," Frontiers in Pharmacology, vol. 10, Feb. 7, 2019 in 14 pages.

Curley et al., "Focused Ultrasound Immunotherapy for Central Nervous System Pathologies: Challenges and Opportunities," Theranostics, vol. 7, No. 15, Jan. 1, 2017, pp. 3608-3623.

Goldwirt et al., "Enhanced brain distribution of carboplatin in a primate model after blood-brainbarrier disruption using an implantable ultrasound device," Cancer Chemotherapy and Pharmacology, Springer Verlag, vol. 77, No. 1, Dec. 8, 2015, pp. 211-216.

Healey et al. "Acoustic cluster therapy: in vitro and ex vivo measurement of activated bubble size distribution and temporal dynamics," Ultrasound in Med Biol. May 1, 2016;42(5): 1145-6611.

Jordao et al., "Antibodies Targeted to the Brain with Image-Guided Focused Ultrasound Reduces Amyloid-? Plaque Load in the TgCRND8 Mouse Model of Alzheimer's Disease," PLOS One, vol. 5, No. 5, May 1, 2010 in 8 pages.

Kinoshita et al., "Targeted delivery of antibodies through the blood-brain barrier by MRI-guided focused ultrasound," Biochemical and Biophysical Research Communications, vol. 340, No. 4, Feb. 24, 2006, pp. 1085-1090.

Kooiman et al. Ultrasound-responsive cavitation nuclei for therapy and drug delivery. Ultrasound Med Biol. Jun. 1, 2020;46(6):1296-1325.

Kurdziel et al., "Human dosimetry and preliminary tumour distribution of 18F-fluoropaclitaxel in healthy volunteers and newly diagnosed breast cancer patients using PET/CT". J Nucl Med. Sep. 1, 2011;52(9):1339-1345.

Lattwein et al., Sonobactericide: an emerging treatment strategy for bacterial infections. Ultrasound Med Biol. Feb. 1, 2020;46(2):193-215.

Mainprize et al., "Blood-Brain Barrier Opening in Primary Brain Tumors with Non-invasive MR-Guided Focused Ultrasound: A Clinical Safety and Feasibility Study," Scientific Reports, vol. 9, No. 1, Dec. 1, 2019 in 7 pages.

Ng et al., "Abstract A099: Acoustic Cluster Therapy enhances the efficacy of chemotherapeutic regimens in patient-derived xenograft mouse models for pancreatic ductal adenocarcinoma," Molecular Cancer Therapeutics, vol. 18, Dec. 1, 2019.

Ryman et al., "Pharmacokinetics of monoclonal antibodies". CPT Pharmacometrics Syst Pharmacol. Sep. 2017;6(9):576-588.

Sontum et al., "Acoustic Cluster Therapy (ACT)—A novel concept for ultrasound mediated, targeted drug delivery." Int J Pharma. Nov. 30, 2015;495(2):1019-1027.

Timko et al., "Remotely triggerable drug delivery systems", Adv Mater. Nov. 24, 2010;22(44): 4925-4943.

Van Wamel et al., Ultrafast microscopy imaging of acoustic clustere therapy bubbles: Activation and oscillation. Ultrasound in Med Biol. Sep. 1, 2022;48(9): 1840-1857.

Wang et al., "Experimental study of tumor therapy mediated by multimodal imaging based on a biological targeting synergistic agent," Intl J Nanomed. Mar. 17, 2020: 1871-1888.

Wei et al., "Focused Ultrasound-Induced Blood-Brain Barrier Opening to Enhance Temozolomide Delivery for Glioblastoma Treatment: A preclinical Study," PLOS One, vol. 8, No. 3, Mar. 1, 2013 in 10 pages.

Zhang et al., "Acoustic Droplet Vaporization for Enhancement of Thermal Ablation by High Intensity Focused Ultrasound," Acard Radiol. Sep. 2011;8(9): 1123-1132.

Zhang et al., "Focused-ultrasound Mediated Anti-Alpha-Synuclein Antibody Delivery for the Treatment of Parkinson's Disease," 2018 IEEE International Ultrasonics Symposium, Oct. 22, 2018, pp. 1-4.

Zheng et al., "Targeted microbubbles with ultrasound irradiation and PD-1 inhibitor to increase antitumor activity in B-cell lymphoma," Nanomedicine, vol. 13, No. 3, Feb. 1, 2018, pp. 297-311.

Combined Search and Examination Report received in UK Patent Application No. GB2104590.1 dated Sep. 27, 2021 in 6 pages.

Combined Search and Examination Report received in UK Patent Application No. GB2105691.6 dated Oct. 7, 2021 in 5 pages.

Duck, "Acoustic Dose and Acoustic Dose-Rate", Ultrasound Med. Biol., vol. 35, No. 10, Oct. 2009, pp. 1679-1685.

Lukka et al., "High-intensity Focused Ultrasound for Prostate Cancer: a Systematic Review", Clinical Oncology, vol. 23, 2011, pp. 117-127.

Meakins et al., "Longwave ultrasound and conductive heating increase functional ankle mobility in asymptomatic subjects", Physical Therapy in Sport, vol. 7, Issue 2, May 2006, pp. 74-80.

TREATMENT OF PANCREATIC CANCER

FIELD OF THE INVENTION

The present invention relates to ultrasound mediated delivery of therapeutic agents to the pancreas, and particularly for treatment of pancreatic cancer such as pancreatic ductal adenocarcinoma (PDAC). Thus, the invention provides a cluster composition and a pharmaceutical composition, for use in delivery of therapeutic agents and for use in the treatment of pancreatic cancer, e.g. PDAC.

BACKGROUND OF THE INVENTION

Pancreatic ductal adenocarcinoma (PDAC), which has a five-year survival rate of less than 9%, is one of the most lethal types of malignancies. Current clinical treatment regimens include chemotherapy and/or surgery, with or without radiation therapy. Whilst surgery remains the only potential for cure, it is rarely an option due to the often late diagnosis and invasive nature of PDAC. If a tumour is downgraded following treatment allowing for the possibility of surgery, overall survival increases considerably, indicating the importance of tumour volume. PDAC is notoriously resistant to conventional and targeted therapeutic agents. Although the reasons for such broad chemoresistance may be multifactorial, one major mechanism is thought to be the low rate of drug penetration into the tumour bed. One of the main reasons for this extreme drug resistance is the desmoplastic and poorly vascularized stroma that forms a protective barrier around the PDAC cells. Hence, a major limitation in effectively treating such solid tumours using therapeutic agents, such as chemotherapeutics, is the inadequate delivery to the target location whether due to tumour interstitial fluid pressure, lack of vascularisation or perfusion, or the presence of a dense stromal matrix. The stromal microenvironment is a complex structure composed of an extracellular matrix (ECM), activated fibroblasts and myofibroblasts, inflammatory cells and blood and lymphatic vessels that distort the normal architecture of pancreatic tissue. The complex interplay between tumour cells and stroma promotes cancer cell motility, resistance to hypoxia and stromal neo-vascularization. These physical barriers result in inaccessibility to the tumour for most chemotherapeutic agents. As a result, all chemotherapeutic treatments suffer the same fate in vivo, whilst increasing dosage to compensate only exacerbates systemic side effects. Thus, mechanical disruption of the tumour or normalisation of tumour vascularisation to permit enhanced delivery of therapeutics may provide greater clinical promise. Therefore, improved drug delivery may lead to a significant impact on the treatment outcome of chemotherapeutics in patients with PDAC.

Therapeutic options specifically focused on targeted drug delivery in treating solid tumours are currently under investigation, including nanoparticles, molecular targeting, and ultrasound- and microbubble mediated therapy, i.e. sonoporation. Sonoporation is a methodology where gas microbubbles are injected into the vasculature and stimulated by ultrasound (US) to invoke biomechanical effects that increase the permeability of the vascular barrier and extravasation of drug at a specific location. Microbubbles are stabilized gas bubbles (2-3 µm in diameter) that are injected intravascularly and are typically stable for up to 1-2 minutes in vivo with no known side-effects. Upon the application of ultrasound, these microbubbles oscillate and are believed to interact with nearby endothelial/vascular wall cells forming fenestrations via a variety of biomechanical effects. This interaction may permit increased extravasation of drug from the vascular compartment, intracellular drug uptake and also allowing therapeutic agents to penetrate deeper into the tissue than the vascular barrier alone. Whilst this technology show promise, the true potential of sonoporation is limited due to the use of commercially available microbubbles designed and optimised for ultrasound imaging, not therapeutic enhancement. As a result, substantial research is focusing on developing "next-generation" microbubbles optimised for ultrasound mediated, targeted and enhanced therapy. A primary limitation is the size of microbubbles. Being small, the level of biomechanical effects they can exert inside the vascular compartment is limited. Furthermore, physical contact with the endothelial wall is limited and, as the biomechanical effects induced typically decline exponentially with distance from the vessel wall, effectiveness in inducing fenestrations is restricted.

Recently, in WO2015/047103, a concept for ultrasound mediated, targeted delivery is proposed, wherein a microbubble/microdroplet cluster composition is administered alongside a therapeutic agent and where ultrasound insonation of a targeted pathology may lead to an increase in the therapeutic effect versus the therapeutic agent alone. This concept, termed as Acoustic Cluster Therapy (ACT Sonoporation or ACT), has later been investigated in a series of pre-clinical proof of principal and proof of concept studies. For example, S. Kotopoulis et al., Acoustic Cluster Therapy (ACT®) induces transient tumour volume reduction in a subcutaneous xenograft model of pancreatic ductal adenocarcinoma. J Control Release, 245 (2016) 70-80, describes a pre-clinical study where ACT is combined with paclitaxel for treatment of PDAC in mice. Unfortunately, due to several limitations in this study the increase in therapeutic effect over drug alone was marginal with only a minor decrease in tumour growth rate, no improvement in survival time and no complete responders.

Based on the above, there remains a significant unmet need for new and alternative compositions and methods for treatment of subjects with pancreatic cancer, such as PDAC.

BRIEF SUMMARY OF THE INVENTION

It is an objective of the present invention to provide compositions and methods for use in the treatment of subjects with pancreatic cancer, and particularly for treatment of pancreatic ductal adenocarcinoma (PDAC). Based on performed studies, and new planned studies, the applicant has found that the Acoustic Cluster Therapy technology is useful in treatment of PDAC, and that it particularly provides an improved therapeutic effect of co-administered therapeutic agent(s), compared to treating a subject with the therapeutic agent(s) alone.

A pharmaceutical composition including a cluster composition, that enhances delivery of therapeutic agents to the pancreas and treatment of pancreatic cancer, has now been identified. This uses ACT technology to generate large phase shift bubbles in vivo from an administered pharmaceutical composition comprising microbubble/microdroplet clusters, and which facilitates delivery of separate pre-, and/or co-and/or post administered therapeutic agent(s). The method provides a considerable increase in therapeutic effect over the use of the therapeutic agent alone.

In one aspect, the invention provides a pharmaceutical composition for use in a method of treatment of pancreatic cancer, wherein the pharmaceutical composition comprises:

(a) a cluster composition which comprises a suspension of clusters in an aqueous biocompatible medium, where said clusters have a mean diameter in the range 1 to 10 μm, and a circularity <0.9 and comprises:

(i) a first component which comprises a gas microbubble and first stabilizer to stabilize said microbubble; and (ii) a second component which comprises a microdroplet comprising an oil phase and second stabilizer to stabilize said microdroplet, where the oil comprises a diffusible component capable of diffusing into said gas microbubble so as to at least transiently increase the size thereof;

where the microbubbles and microdroplets of said first and second components have opposite surface charges and form said clusters via attractive electrostatic interactions; and (b) a therapeutic agent selected from the group of chemotherapeutic agents and immunotherapeutic agents, or combinations thereof, provided as a separate composition to (a).

The invention further provides a method of treatment of a subject with pancreatic cancer, comprising the step of administering to the subject a pharmaceutical composition comprising;

(a) a cluster composition which comprises a suspension of clusters in an aqueous biocompatible medium, where said clusters have a mean diameter in the range 1 to 10 μm, and a circularity <0.9 and comprises:

(i) a first component which comprises a gas microbubble and first stabilizer to stabilize said microbubble; and (ii) a second component which comprises a microdroplet comprising an oil phase and second stabilizer to stabilize said microdroplet, where the oil comprises a diffusible component capable of diffusing into said gas microbubble so as to at least transiently increase the size thereof;

where the microbubbles and microdroplets of said first and second components have opposite surface charges and form said clusters via attractive electrostatic interactions; and (b) a therapeutic agent selected from the group of chemotherapeutic agents and immunotherapeutic agents, or combinations thereof, provided as a separate composition to (a).

4 with ACT (filled circles). X-axis shows time in days from start of treatment. Treatments were performed at Days 0, 7 and 14.

Figure 4:
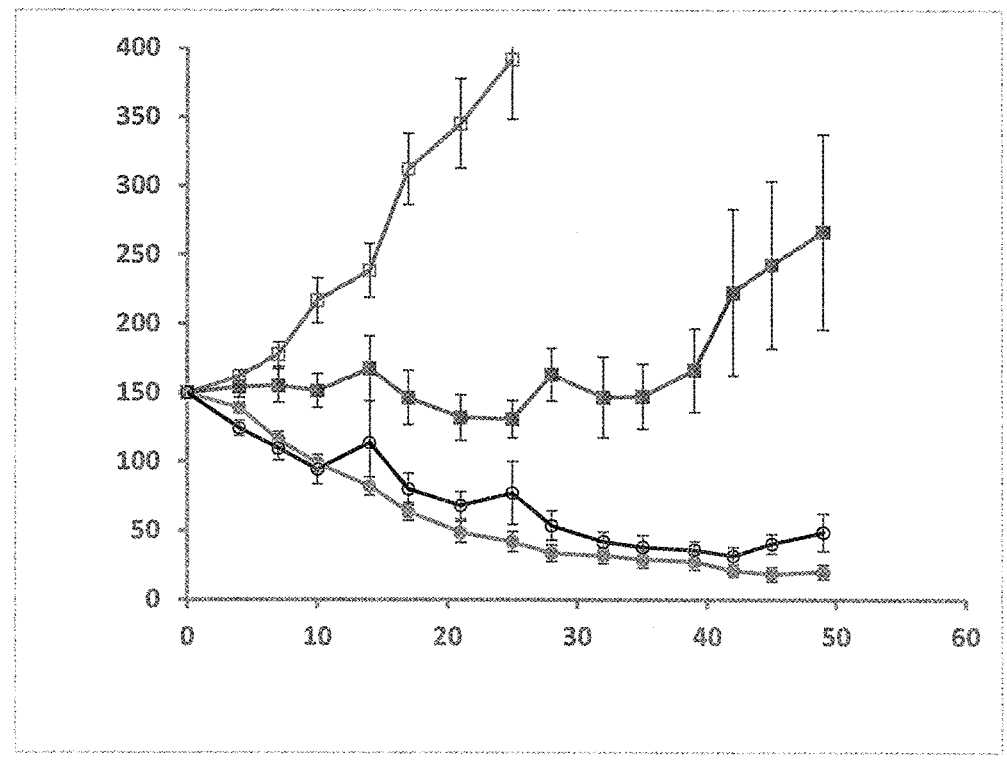

FIG. 4 provides results from the study of Example 2 wherein the Y-axis shows the tumour volume as a function of time for treatment of pancreatic ductal adenocarcinoma in mice with nab-paclitaxel/gemcitabine (filled squares), saline control (open squares), ACT prior to administration of nab-paclitaxel/gemcitabine (open circles) and nab-paclitaxel followed by ACT (filled circles). X-axis shows time in days from start of treatment. Treatment at Days 0, 7 and 14.

Figure 5:
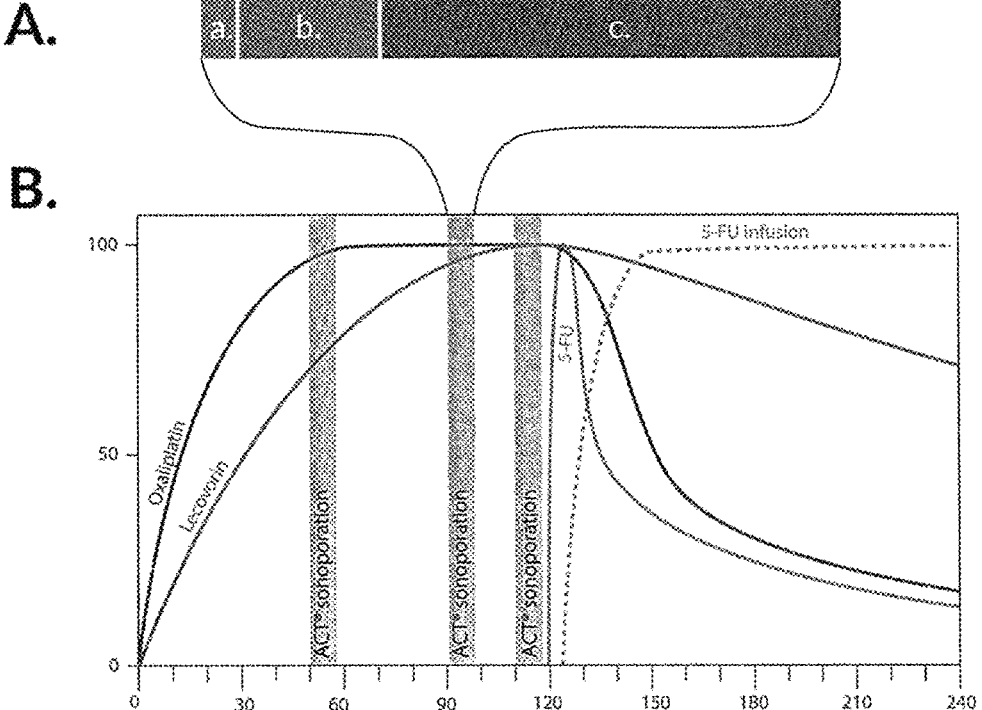

FIG. 5 provides a graph from an example of ACT treatments performed during administration of the chemotherapeutic regime FOLFOX (leucovorin and oxaliplatin infusion for 2 h, followed by fluorouracil (5-FU) bolus injection at 2 h), followed by fluorouracil infusion for 48 h. Panel A: each ACT treatment comprises a.; injection of cluster composition followed by b.: activation of clusters with regular medical imaging US insonation and c.: enhancement with low frequency US insonation. Panel B: The Y-axis shows blood plasma concentration, relative to peak. The X-axis show time in minutes. Three ACT procedures are performed at approx. 50 minutes, 80 minutes and 110 minutes in order to cover all three drugs.

Figure 6:
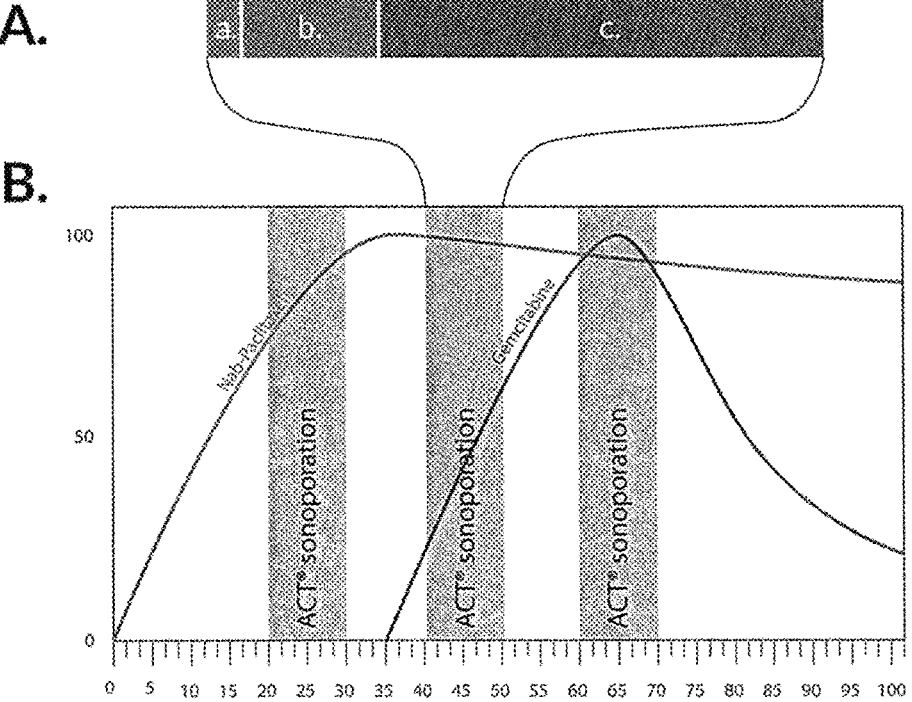

FIG. 6 provides a graph from an example of treatment schedule with chemotherapy combination regime gemcitabine and nab-paclitaxel: 30 minutes hour infusion of nab-paclitaxel followed by 30 minutes infusion of gemcitabine. The ACT procedure is applied three times during the chemotherapy administration, as indicated by grey ACT® sonoporation bars. Panel A: each ACT procedure consists of a.; injection of the cluster composition, b.: activation of clusters with 60 second of regular medical imaging ultrasound insonation and c.; enhancement step with 5 minutes of 400 to 600 kHz ultrasound insonation. Panel B: Y-axis showing plasma concentration of administered chemotherapeutics in percent of peak and X-axis showing time in minutes.

Figure 7:
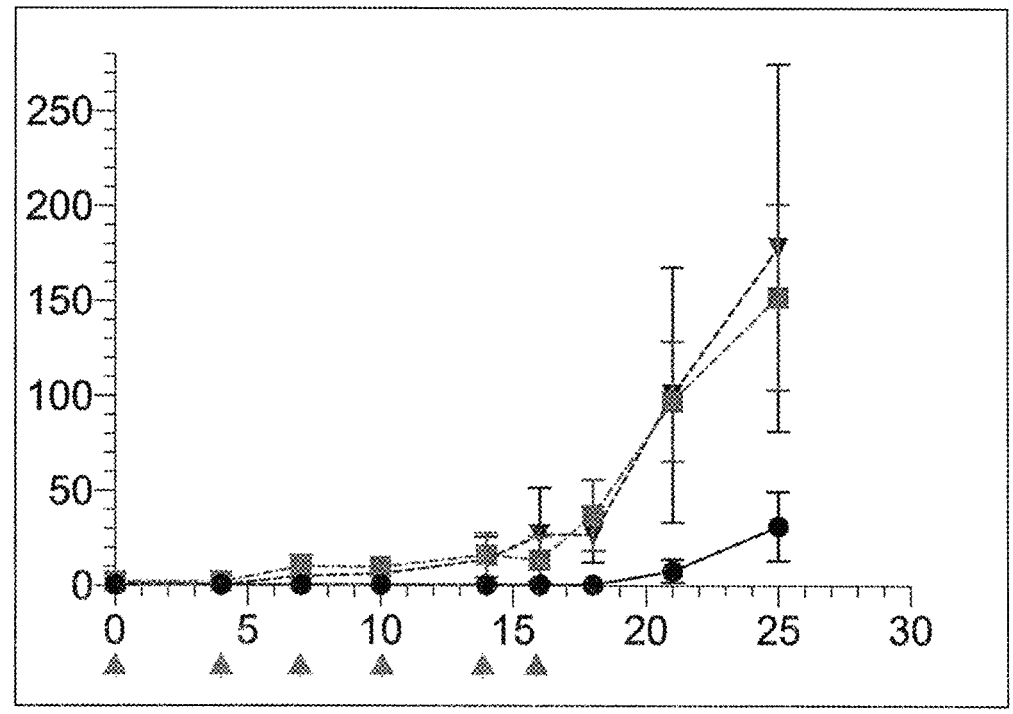

FIG. 7 provides results from the study of Example 3 wherein the Y-axis shows tumour volume as a function of time for treatment of Hepatocellular Carcinoma (HCC) in mice with an oncolytic reovirus (filled triangles), saline control (filled squares) and oncolytic reovirus in combination with ACT (filled circles). X-axis shows time from start of treatment. Grey triangles below the X-axis indicate treatment days.

DETAILED DESCRIPTION OF THE INVENTION

Definitions

As used herein, Activated Cluster Therapy (ACT), which is further defined below, comprises the administration of a cluster composition (cf. definition below) in conjunction with at least one therapeutic agent (chemotherapeutic or immunotherapeutic agent), and subsequent application of ultrasound to a targeted pathological region (e.g. tumour).

As used herein, "subject" means any human, or non-human animal individual selected for treatment or therapy, and encompasses, and may be limited to, a patient, particularly to a human patient diagnosed with pancreatic cancer, such as PDAC.

The phrase "therapeutically effective amount" as used herein means the amount of therapeutic agent which is effective for producing the desired therapeutic effect in a subject at a reasonable benefit/risk ratio applicable to any treatment.

The term 'microbubble' or 'regular, contrast microbubble' is used in this text to describe microbubbles with a diameter in the range from 0.2 to 10 microns, typically with a mean diameter between 2 to 3 μm. 'Regular, contrast microbubbles' include commercially available agents such as Sonazoid (GE Healthcare), Optison (GE Healthcare), Sonovue (Bracco Spa.), Definity (Lantheus Medical Imagin), Micromarker (VisualSonics Inc.) and Polyson L (Miltenyi Biotec GmbH).

The term HEPS/PFB microbubble is used in this text to describe the microbubbles formed by reconstituting a 1st component (as provided in Example 1) with 2 mL of water.

The terms 'phase shift bubbles', 'large, phase shift bubbles, 'large, activated bubbles' and 'activated bubbles' in this text is used to describe the large (>10 μm) bubbles that form after ultrasound (US) induced activation of the cluster composition.

The term 'microdroplet' is used in this text to describe emulsion microdroplets with a diameter in the range from 0.2 to 10 microns.

'Insonation' or 'US insonation' are terms used to describe exposure to, or treatment with, ultrasound.

The term "regular medical imaging ultrasound" is used to describe ultrasound from of the shelf US scanners and probes intended for medical imaging. I.e. at a frequency between 1 to 10 MHz and an MI of <1.9, preferably <0.7 and more preferably <0.4.

The term 'deposit tracer' is used in this text in relation to the activated phase shift bubbles, in the sense that the temporary mechanical trapping of the large bubbles in the microcirculation implies that the regional deposition of phase shift bubbles in the tissue will reflect the amount of blood that flowed through the microcirculation of the tissue at the time of activated bubble deposition. Thus, the number of trapped 'deposited' phase shift bubbles will be linearly dependent on the tissue perfusion at the time of deposition.

The term 'phase shift (process)' is used in this text to describe the phase transition from the liquid to gaseous states of matter. Specifically, the transition (process) of the change of state from liquid to gas of the oil component of the microdroplets of the cluster composition upon US insonation.

The term 'bi-phasic' refers to a system comprising of two phases of state, specifically liquid and gaseous states, such as the microbubble (gas) and microdroplet (liquid) components of the cluster composition.

In this text the terms "therapy delivery/therapeutic agent (s)" and "drug delivery/drug(s)" are both understood to include the delivery of drug molecules, nanoparticles and nanoparticle delivery systems, and liposomal delivery systems, including at least one therapeutically active agent.

The term '1 st component' (or first component, or C1) is used in this text to describe the dispersed gas (microbubble) component. The term '2nd component' (or second component, or C2) is used in this text to describe the dispersed oil phase (microdroplet) component comprising a diffusible component.

The term 'cluster composition' is used in this text to describe a composition resulting from a combination, such as mixing, of the 1st (microbubble) component and the 2nd (microdroplet) component. Hence, the cluster composition, with characteristics as further described herein, refers to the formulated composition ready for administration to a subject, and for use in the Activated Cluster Therapy.

The term "diffusible component" is used in this text to describe a chemical component of the oil phase of the 2nd component that is capable of diffusion in vivo into the microbubbles in the 1 st component, transiently increasing its size.

The term "pharmaceutical composition" used in this text has its conventional meaning, and in particular is in a form suitable for mammalian administration. The composition preferably comprises two separate compositions; The cluster composition (a), and the therapeutic agent (b), which are both suitable for mammalian administration such as via parenteral injection, intraperitoneal injection or intramuscular injection, either by the same or different administration routes. By the phrase "in a form suitable for mammalian administration" is meant a composition that is sterile, pyrogen-free, lacks compounds which produce excessive toxic or adverse effects, and is formulated at a biocompatible pH (approximately pH 4.0 to 10.5). Such a composition is formulated so that precipitation does not occur on contact with biological fluids (e.g. blood), contain only biologically compatible excipients, and is preferably isotonic.

The term 'Sonometry (system)' in this text refers to an in-vitro measurement system to size and count activated phase shift bubbles dynamically using an acoustic technique.

The term 'Reactivity' is used in this text to describe the ability of the microbubbles in the 1st component and the microdroplets in the 2nd component to form microbubble/microdroplet clusters upon mixing. Coulter counting is suitable for quantification of microbubble and microdroplet concentration and size distribution in C1 and C2, and for characterization of particles in the cluster composition (drug product, DP). Reactivity (R) of the cluster composition defined as;

$$R=(C_{C1}+C_{C2}-C_{DP})\cdot100/(C_{C1}+C_{C2})$$

Where $CC_1$, $C_{C2}$ and $C_{DP}$ are the number concentration observed in C1, C2 and DP, respectively. The Reactivity is hence a measure of how many of the individual microbubbles and microdroplets in C1 and C2 that are contained in cluster form in the DP. The Reactivity is also correlated to how large these clusters are (i.e. how many individual microbubbles and microdroplets comprises a single cluster). From Coulter analysis of C1, C2 and DP, the Reactivity can easily be calculated.

The terms 'microbubble/microdroplet cluster" or "cluster" in this text refers to groups of microbubbles and microdroplets permanently held together by electrostatic attractive forces, in a single particle, agglomerated entity. The term 'clustering' in this text refers to the process where microbubbles in the $1^{st}$ component and microdroplets of the $2^{nd}$ component form clusters.

Within medical ultrasound, acoustic power is normally described by "the Mechanical Index" (MI). This parameter is defined as the peak negative pressure in the ultrasound field (PNP), de-rated by 0.3 dB/cm/MHz divided be the square root of the centre frequency of the ultrasound field in MHz ($F_c$) [American Institute of Ultrasound in Medicine. Acoustic Output Measurement Standard for Diagnostic Ultrasound Equipment. 1st ed. 2nd ed. Laurel, Md.: American Institute of Ultrasound in Medicine; 1998, 2003].

$$MI = \frac{PNP}{\sqrt{F_C}}.$$

Regulatory requirements during medical US imaging are to use a MI less than 1.9. During US imaging with microbubble contrast agents, an MI below 0.7 is recommended to avoid detrimental bio-effects such as micro-haemorrhage and irreversible vascular damage and using an MI below 0.4 is considered "best practise".

The term 'activation' or "activation step" in the context of the ACT procedure in this text, refers to the induction of a phase shift of microbubble/microdroplet clusters by ultrasound (US) insonation, i.e. the generation of large, activated bubbles.

The term frequency is defined as number of (ultrasound) cycles per second (Hz). When used herein the term designate the centre frequency of the applied sound field.

The term "enhancement" or "enhancement step", in the context of the ACT procedure in this text, refers to the induction of volume oscillations of the large, activated bubbles and ensuing biomechanical effects, by US insonation.

DETAILS OF THE INVENTION

The invention provides a cluster composition for use in a method of treatment of pancreatic cancers, and particularly subjects with pancreatic ductal adenocarcinoma (PDAC). The invention uses ACT technology to generate large phase shift bubbles in vivo from an administered pharmaceutical composition comprising microbubble/microdroplet clusters, and which facilitates delivery and uptake of separate pre-, and/or co- and/or post administered therapeutic agent(s). The therapeutic effect of the therapeutic agent is considerably increased compared to administration of the agent alone, due to biomechanical mechanisms in the microvasculature, as further explained below. The activated phase shift bubbles are approximately 10 times larger in diameter than typical, regular contrast microbubbles.

Pancreatic cancers include any type of cancer of the pancreas including PDAC, non-adenocarcinomas, and neuroendocrine tumours, and is preferably PDAC.

PDAC is a cancer form wherein an epithelial tumour arises from the cells of the pancreatic duct or ductules, for which it is named. The pancreatic duct(s) serve as the conduit through which digestive enzymes and bicarbonate ion produced in acinar cells reach the small intestine. Ductal cells and acinar cells together represent the "exocrine" pancreas, from which the vast majority of pancreatic neoplasms arise. Adenocarcinomas is defined as neoplasia, i.e. abnormal and excessive growth, of epithelial tissue. Once a diagnosis of PDAC is confirmed or highly suspected, an attempt to stage the tumour is typically made. This is achieved primarily through triphasic CT scan of the abdomen. The 7th edition of the American Joint Committee on Cancer (AJCC) Pancreas Cancer Staging follows the standard "TNM" (Tumour size, lymph Node status, Metastasis) format and is commonly used to stage the tumour and determine prognosis. In stage 0, abnormal cells are found in the lining of the pancreas. These abnormal cells may become cancer and spread into nearby normal tissue. Stage 0 is also called carcinoma in situ. In stage I, cancer has formed and is found in the pancreas only. Stage I is divided into stages IA and IB, depending on the size of the tumour. Stage IA: The tumour is 2 centimetres or smaller. Stage IB: The tumour is larger than 2 centimetres but not larger than 4 centimetres. Stage II is divided into stages IIA and IIB, depending on the size of the tumour and where the cancer has spread. Stage IIA: The tumour is larger than 4 centimetres. Stage IIB: The tumour is any size and cancer has spread to 1 to 3 nearby lymph nodes. In stage III, the tumour is any size and cancer has spread to four or more nearby lymph nodes; or the major blood vessels near the pancreas. In stage IV, the tumour is any size and cancer has spread to other parts of the body, such as the liver, lung, or peritoneal cavity (the body cavity that contains most of the organs in the abdomen). Recurrent pancreatic cancer is cancer that has recurred after it has been treated. The cancer may come back in the pancreas or in other parts of the body.

The composition for use, and the method of treatment, of the invention may be useful in all stages of PDAC and may be used in treatment of one or more of the stages 0, I, II, III or IV. In one embodiment, the pharmaceutical composition according to the invention is for treatment of PDAC in either of the stages 0, I, II or IV. In one embodiment, the pharmaceutical composition is for treatment of PDAC in the earlier stages, e.g. for treatment of PDAC in stages 0, I or II.

The invention provides a pharmaceutical composition comprising a cluster composition, for use in a method of delivery of therapeutic agents to the pancreas and treatment of pancreatic cancer, wherein the method includes phase shift technology to generate large phase shift bubbles in vivo from an administered cluster composition, and which facilitates delivery and uptake of separately administered therapeutic agent(s). The composition for use and the method of the invention potentiate the therapeutic effect of the separately co-administered therapeutic agent, providing an improved therapeutic outcome, compared to treatment without the use of the compositions of the invention.

Acoustic Cluster Therapy (ACT) is a novel technology that utilizes microbubbles, and more particularly microbubble/microdroplet clusters, activated by the application of ultrasound, to create localized openings or fenestrations in the tumour vasculature, leading to a transient increase in vascular permeability and thereby allowing drugs to better penetrate the tumour bed. The current invention is partly based on findings from a pre-clinical study, wherein the applicant has investigated the activity of ACT in enhancing the therapeutic effects of clinically used chemotherapeutic regimens in patient-derived xenograft (PDX) mouse models for PDAC. The applicant has found that the ACT concept is an effective way to overcome biological barriers for improved uptake of therapeutic agents. This has been found to be particularly beneficial for treatment of pancreatic cancers, and particularly PDAC, because of the generally low rate of drug penetration into the tumour bed, due to the desmoplastic and poorly vascularized stroma that forms a protective barrier around the PDAC cells. Even though Kotopoulis et al. briefly notes the potential use of ACT for treatment of Stage III PDAC, it does not suggest how such use could be implemented, it does not point towards the very specific treatment benefit this disease could entail (as shown in the Examples herein), using ACT to overcome the stromal desmoplasia, nor does it suggest treatment of earlier or later stages of the disease. Furthermore, Kotopoulis et al. only points to one specific small molecule drug and does not teach the use of the ACT concept with alternative, larger molecules/constructs therapeutic agents such as liposomal formulations of drugs or use of immunotherapy agents such as e.g. oncolytic viruses or check-point inhibitors.

When referring to the ACT technology for the current invention, this includes the administration of a premixed cluster composition as further explained below, in addition to the separate administration of a therapeutic agent. The therapeutic agent is administered according to standard of care, i.e. according to the respective Summary of Product Characteristics (SmPC). In one embodiment of the invention, this includes the use of a cluster formulation combining negatively charged microbubbles with positively charged microdroplets prior to administration to a subject. The administered clusters can be activated by ultrasound. A mixture of these microbubbles and microdroplets results in small microbubble-microdroplets clusters held together by electrostatic forces. The microdroplets typically comprise an oil component that has a boiling temperature of <50° C., and low blood solubility. The cluster composition, i.e. a dispersion, is intended for administration with a drug, i.e. with a therapeutic agent. When the clusters of the cluster composition are insonated with ultrasound the oscillating microbubbles initiate an instant vaporisation (phase-shift) of the attached microdroplet. The enlarged resulting bubbles have been shown to form in capillary sized vessels in vivo and can be excited by low frequency US to induce biomechanical effects that facilitate extravasation and increase drug penetration in the insonated tissue.

Hence, drug delivery to the pancreas and treatment of pancreatic cancer according to the invention is achieved by the use of a two component, bi-phasic microbubble/microdroplet formulation system (i.e. the cluster composition) where microbubbles in a first component, via electrostatic attraction, are physically attached to micron sized emulsion microdroplets in a second component prior to administration. The composition for use in a method of treatment of PDAC, according to the invention, provides improved uptake of therapeutic agents, resulting in a beneficial treatment, including e.g. a reduction in tumour volume. Mixing the first component with the second component prior to administration is a pre-requisite for the efficient formation of the microbubble/microdroplet clusters and that the cluster composition can be stable at ambient conditions. The clusters are readily activated in-vivo with low power, regular medical imaging ultrasound, i.e. with an MI of less than 1.9, preferably less than 0.7 and most preferably less than 0.4, which induce a liquid-to-gas transition (phase shift) of the diffusible component. The therapeutic agent, i.e. a chemotherapeutic agent or an immunotherapeutic agent, or combinations thereof, is administered separately according to its approved SmPC. The large, activated bubbles are temporarily embedded in the microvasculature of the insonated tissue and facilitate drug uptake to the pancreatic target tissue by further application of low power, low frequency ultrasound. The activated phase shift bubbles are approximately 10 times larger in diameter than typical microbubbles, resulting in:

transient deposition/trapping of activated bubbles in the microvasculature of the targeted (i.e. insonated) pathology;

close contact between the activated bubbles and the endothelium;

compared to regular contrast microbubbles; orders of magnitude larger biomechanical effects during post activation US treatment, avoiding inertial cavitation mechanisms.

The cluster composition, i.e. the combination of the first and second components, comprises clusters of gas microbubbles and oil microdroplets, i.e. is a suspension or dispersion of individual microbubbles and microdroplets in the form of stable microbubble/microdroplet clusters. Analytical methodologies for quantitative detection and characterisation of said clusters are described in Example 1. In this text, the term "clusters" refers to groups of microbubbles and microdroplets permanently held together by electrostatic attractive forces, in a single particle, agglomerated entity. The content and size of the clusters in the cluster composition is essentially stable over some time (e.g. >1 h) after combining the first and second components in vitro, i.e. they do not spontaneously disintegrate, form larger aggregates or activate (phase shifts) spontaneously, and are essentially stable over some time after dilution, even during continued agitation. It is hence possible to detect and characterize the clusters in the cluster composition with various analytical techniques that require dilution and/or agitation. Furthermore, the stability of the cluster composition allows for performing the necessary clinical procedures (e.g. reconstitution, withdrawal of dose and administration). The first and second components, and the cluster composition, are prepared according to Good Manufacturing Practice (GMP).

After combining the two components (in vitro), e.g. by reconstituting a lyophilized microbubble component with a microdroplet component in the form of an emulsion, the prepared cluster composition according to the invention display an in-use stability which is suitable for its intended use and display stable characteristics for a suitable time window for administration, such as more than 1 h or preferably more than 3 h from combining the components. The cluster composition is to be administered to the subject within this time window.

Each cluster in the cluster composition comprises at least one microbubble and one microdroplet, typically 2-20 individual microbubbles/microdroplets, and a cluster typically has a mean diameter in the range of 1 to 10 µm and can hence flow freely in the vasculature. They are further characterized and separated from individual microbubbles and microdroplets by a circularity parameter. The circularity of a two-dimensional form (e.g. a projection of a microbubble, microdroplet or microbubble/microdroplet cluster) is the ratio of the perimeter of a circle with the same area as the form, divided by the actual perimeter of the form. Accordingly, a perfect circle (i.e. a two-dimensional projection of a spherical microbubble or microdroplet) has a theoretical circularity value of 1, and any other geometrical form (e.g. projection of a cluster) has a circularity of less than 1. Said clusters of the invention have a circularity <0.9. The definition of circularity parameter is further provided in WO2015/047103.

According to the invention, compositions comprising clusters with a mean size in the range of 1-10 µm, and particularly 3-10 µm, and defined by a circularity of <0.9 are considered particularly useful, as demonstrated in the examples. In one embodiment the mean cluster diameter is in the range of 3-10 µm, and preferably 4-9 µm, more preferably 5-7 µm. Clusters in this size range are free-flowing in the vasculature before activation, they are readily activated by US insonation and they produce activated bubbles that are large enough to deposit and lodge temporarily in the microvasculature, such as e.g. in pancreatic tissue or pancreatic cancerous tissue. The microbubbles in the clusters permit efficient energy transfer of ultrasound energy in the diagnostic frequency range (1-10 MHz), i.e. upon activation, and allow vaporisation (phase shift) of the emulsion microdroplets at low MI (under 1.9 and preferably under 0.7 and more preferably under 0.4, but more than 0.1) and diffusion of the vaporized liquid into the microbubbles and/or fusion between the vapour bubble and the microbubble. The activated bubble then expands further from the inwards diffusion of matrix gases (e.g. blood gases) to reach a volume weighted, median diameter of more than 10 µm, but less than 40 µm.

The formation of theses clusters, i.e. by preparing a cluster composition from the first component and the second component prior to administration, is a prerequisite for an efficient phase shift event and their number and size characteristics are strongly related to the efficacy of the composition, i.e. its ability to form large, activated (i.e. phased shifted) bubbles in-vivo, and has been found to be a prerequisite for its intended functionality in-vivo. The number and size characteristics can be controlled through various formulation parameters such as, but not limited to; the strength of the attractive forces between the microbubbles in the first component and the microdroplets in the second component (e.g. the difference in surface charge between the microbubbles and microdroplets): the size distribution of microbubbles and microdroplets: the ratio between microbubbles and microdroplets: and the composition of the aqueous matrix (e.g. pH, buffer concentration, ionic strength). When the cluster composition has been prepared and is to be administered, the mean circular equivalent diameter of the clusters formed should preferably be larger than 3 µm, more preferably between 5 to 7 µm, but smaller than 10 µm. The concentration of clusters between 3 to 10 µm in the combined preparation (cluster composition) should preferably be more than million/mL, more preferably more than 20 million/mL. As shown in Example 1, a cluster composition for use according to the invention had a cluster concentration of 40-44 million/mL with a mean diameter of 5.8-6.2 µm measured 0-3 hours after mixing of the first and second components. In one embodiment, based on the results shown in Tables 5 and 6 of applicant's WO2015/047103, the composition for administration should comprise at least 0.6 million/ml of clusters with a diameter between 5-10 um. In another embodiment, the cluster concentration, of clusters in size range 1-10 µm, should be at least around 25 million/ml.

The size of the activated bubbles (in vivo) can be engineered by varying different formulation parameters of the $1^{st}$ and $2^{nd}$ components and the size characteristics of the clusters as prepared (see Example 1). The clusters are activated to produce large bubbles by application of external ultrasound energy, after administration, such as from a clinical ultrasound imaging system, under imaging control. The large phase shift bubbles produced are typically of a diameter of 10 µm or more. Low MI energy levels, which are well within the diagnostic imaging exposure limits (MI<1.9), are sufficient to activate the clusters which make the technology significantly different from the other phase transition technologies available (e.g. acoustic microdroplet vaporisation (ADV)). Due to the large size of the activated bubbles, they temporarily lodge in the microvasculature and can be spatially localised in a tissue or organ of interest, such as of the pancreas or, more preferably, a cancerous tissue (e.g. a tumour) in the pancreas, by spatially localised application of the ultrasound energy to activate the clusters. Hence, after administration of the cluster composition, the clusters are activated within, at or near the pancreas by application of ultrasound energy towards the abdomen and the site of the pancreas. The large, activated bubbles produced (10 µm or more in diameter) have acoustic resonances at low ultrasound frequency (1 MHz or less).

It will be appreciated that for the composition for use and method of the invention, a further insonation of the large activated bubbles with the application of low frequency ultrasound further enhances the uptake of the therapeutic agent(s). Hence, it has been found that the application of low frequency ultrasound, close to the resonance frequencies of the large, activated bubbles, can be used to produce mechanical and/or thermal bio-effect mechanisms to increase the permeability of the vasculature and/or sonoporation and/or endocytosis of cancerous tissue in the pancreas and hence increase delivery and retention of the therapeutic agent to the targeted tissue. Hence, frequency components in the range 0.05 to 2 MHz, preferably in the range 0.1 to 1.5 MHz, more preferably in the range 0.1 to 1.0 MHz, even more preferably in the range of 0.2 to 1 MHz, and most preferably in the range of 0.4 to 0.6 MHz, such as particularly 0.33 to 0.65 MHz are used in the further insonation to enhance uptake. Surprisingly, a larger therapeutic benefit has been found when the activated bubbles are insonated to induce enhanced uptake by applying ultrasound e.g. in the range of 0.4 to 0.6 MHz, e.g. 500 Hz as used in the Examples. And hence problems due to stromal desmoplasia are overcome. The ultrasound guidance has been found to allow the therapeutic agent to better penetrate the tumour bed of the pancreas. The MI for this enhancement step is preferably below 0.5, more preferably below 0.4, and most preferably below 0.3 but above 0.15, preferably above 0.2. If the MI applied during the enhancement step is lower than 0.2 it is expected that the biomechanical effects generated will be insufficient and, hence, reduce the therapeutic benefit significantly.

It should be appreciated that, whereas the direct mechanism of action, i.e. the produced mechanical and/or thermal bio-effect increases delivery and enhancing distribution of the therapeutic agent, the nature of these bio-mechanical effects is a direct result of the chemical attributes of the cluster composition, i.e. a result of the chemical composition and properties of the clusters. For example, the longevity of a gas bubble in an aqueous matrix is inversely proportional to the solubility and diffusion coefficient of the gas in the matrix, and proportional to the density of the gas. Hence, a bubble made from a heavy gas with low solubility and diffusivity will grow bigger and last longer than a bubble made from a light gas with high solubility and diffusivity. As an example, a 5 µm microbubble of perfluorobutane will last 500 times longer in water than a 5 µm microbubble of air. The chemical composition of the microdroplet component will hence govern the longevity of the activated bubbles in-vivo and, hence, the level of bio-mechanical force that can be induced and the therapeutic effect level that can be achieved with the ACT procedure. From this, perfluorated oils will be particularly useful for use in microdroplets of the second component, as gases from such are very low in water solubility and diffusivity, and high in density.

If comparing the compositions and methods of the invention with methods wherein free-flowing, regular contrast microbubbles are used, the large phase shift microbubbles generated in vivo from the administered clusters of the current invention are entrapped in a segment of the vessels and the activated bubble surface is in close contact with the endothelium. In addition, the volume of an activated bubble is typically 1000 times that of a regular microbubble. At equal Mechanical Index (MI), insonated at a frequency close to resonance for both bubble types (0.5 MHz for phase shift microbubbles and 3 MHz for regular contrast agent microbubbles) it has been shown that the absolute volume displacement (i.e. biomechanical force exerted) during oscillations are three orders of magnitude larger with the phase shift bubbles than with a regular contrast microbubble. Hence, insonation of phase shift bubbles will produce completely different levels of bio-mechanical effects, with significantly larger effect size and penetration depth than during insonation of regular contrast microbubbles. The bio-effects observed with free-flowing, regular contrast microbubbles are likely dependent upon cavitation mechanisms, with ensuing safety concerns such as micro-haemorrhage and irreversible vascular damage.

The larger phase shift bubbles from the clusters however, can be oscillated in a softer manner (lower MI, e.g. <0.4), avoiding cavitation mechanisms, but still induce sufficient mechanical force to enhance the uptake of drug from the vasculature and into the pancreatic target tissue. The trapping of the large phase shift bubbles will also act as a deposit tracer. This further allows quantification of the number of activated clusters and perfusion of the tissue and allows contrast agent imaging of the tissue vasculature to identify the spatial extent of the pathology to be treated.

The chemical composition of the administered clusters, and the processes taking place during activation of the clusters, are crucial for the effect of the clusters. For instance, chemistry of the encapsulated oil droplet influences the amount of activated bubbles that deposits upon US insonation as well as their longevity in-vivo. Physicochemical attributes of the oil, such as vapour pressure, boiling point and water solubility all correlate with the amount of activated bubbles that deposit and the time they remain deposited. For a C4-C6 homologue, perfluorated hydrocarbon chain, the amount of activated bubbles and their longevity increase with the length of the chain, as the water solubility and vapour pressure decrease and the boiling point increases. Further it should be noted that the activated large bubbles of the clusters act mechanically on the cells of the vasculature, potentially generating biochemical signals, leading to an increased uptake of the therapeutic agent.

The cluster composition is engineered to cluster and phase shift in a controlled manner. When exposed to ultrasound, e.g. standard medical imaging frequency and intensity, at the targeted pancreatic pathology, the microbubble of the administered cluster composition transfers acoustic energy to the attached oil microdroplets and may act as an evaporation seed, or merge with the microbubble so that the oil undergoes a liquid-to-gas phase shift (vaporisation). The resulting bubble undergoes an initial rapid expansion due to vaporisation of the oil, followed by a slower expansion due to inward diffusion of blood gases, and temporarily blocks the microcirculation (metarteriole and capillary network) for approximately 1 minute or more, preferably 2-3 minutes or more, most preferably 3-6 minutes or more. In the method of the invention, or in the pharmaceutical composition for use, a therapeutic agent is further administered to the subject, such as being co-administered or pre-administered or post-administered with the cluster composition. The clusters are activated to produce large bubbles by application of external ultrasound energy, and these are trapped in the microvasculature of the tumour (e.g. in the pancreas). Further application of low frequency ultrasound after trapping facilitates extravasation of the therapeutic agent to the targeted tissue of the pancreas. Hence, the major limitation of existing technology in effectively treating the solid tumours of the pancreas, due to inadequate delivery to the target location, whether due to tumour interstitial fluid pressure, lack of vascularisation or perfusion, or the presence of a dense stromal matrix, can be overcome by the technology of the current invention, as it has been found that the accessibility to the tumour for the therapeutic agent is considerably increased.

The First Component of the Cluster Composition:

The first component comprises a gas microbubble and a first stabilizer to stabilize the microbubble. The first component is hence an injectable aqueous medium comprising dispersed gas and material to stabilize the gas. The microbubbles may be similar to conventional ultrasound contrast agents that are on the market and approved for use for several clinical applications such as Sonazoid, Optison, Definity or Sonovue, or similar agents used for pre-clinical application such as Micromarker and Polyson L. Any biocompatible gas may be present in the gas dispersion, the term "gas" as used herein including any substances (including mixtures) at least partially, e.g. substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Preferably, the gas is a halogenated gas, and more preferably a perfluorinated gas. Advantageously at least some of the halogen atoms in halogenated gases are fluorine atoms; thus, biocompatible halogenated hydrocarbon gases may, for example, be selected from bromochlorodifluoromethane, chlorodifluoromethane, dichlorodifluoro-methane, bromotrifluoromethane, chlorotrifluoromethane, chloropenta-fluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethyl-cyclobutanes, perfluorocyclopentane, perfluoromethyl-cyclopentane, perfluorodimethyl-cyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether.

The use of perfluorinated gases, for example sulphur hexafluoride and perfluorocarbons such as perfluoropropane, perfluorobutanes, perfluoropentanes and perfluorohexanes, are particularly advantageous in view of the recognised high stability in the bloodstream of microbubbles containing such gases. In one embodiment, the gas of the first component is selected from the group of sulphur fluorides and halogenated low molecular weight hydrocarbons (e.g. containing up to 7 carbon atoms). Other gases with physicochemical characteristics which cause them to form highly stable microbubbles in the bloodstream may likewise be useful. Most preferably, the dispersed gas comprises sulphur hexafluoride, perfluoropropane, perfluorobutane, perfluoropentane, perflurohexane (i.e. a C3-6 perfluorocarbon), nitrogen, air or a mix thereof. Even more preferably, the dispersed gas comprises sulphur hexafluoride, perfluoropropane, or perfluorobutane, or mixture there. And even more preferably, the dispersed gas is perfluorobutane.

The dispersed gas may be in any convenient form, for example using any appropriate gas-containing ultrasound contrast agent formulation as the gas-containing component such as Sonazoid, Optison, Sonovue or Definity or preclinical agents such as Micromarker or PolySon L. The first component will also contain material in order to stabilize the microbubble dispersion, in this text termed 'first stabilizer'. Representative examples of such formulations include microbubbles of gas stabilized (e.g. at least partially encapsulated) by a first stabilizer such as a coalescence-resistant surface membrane (for example gelatin), a filmogenic protein (for example an albumin such as human serum albumin), a polymer material (for example a synthetic biodegradable polymer, an elastic interfacial synthetic polymer membrane, a microparticulate biodegradable polyaldehyde, a microparticulate N-dicarboxylic acid derivative of a polyamino acid-polycyclic imide), a non-polymeric and non-polymerisable wall-forming material, or a surfactant (for example a polyoxyethylene-polyoxypropylene block copolymer surfactant such as a Pluronic, a polymer surfactant, or a film-forming surfactant such as a phospholipid). Preferably, the dispersed gas is in the form of phospholipid-, protein- or polymer-stabilized gas microbubbles. Hence, in one embodiment, the first stabilizer is selected from the group of phospholipids, proteins and polymers. A particularly useful first stabilizer is selected from the group of surfactants which include phospholipids comprising molecules with net overall negative charge, such as naturally occurring (e.g. soya bean or egg yolk derived), semisynthetic (e.g. partially or fully hydrogenated) and synthetic phosphatidyl-serines, phosphatidylglycerols, phosphatidylinositols, phosphatidic acids and/or cardiolipins. Alternatively, the phospholipids applied for stabilization may carry an overall neutral charge and be added a negative surfactant such as a fatty acid, e.g. phosphatidylcholine added palmitic acid, or be a mix of differently charged phospholipids, e.g. phosphatidylethanolamines and/or phosphatidylcholine and/or phosphatidic acid. For the first stabilizer, i.e. stabilizing the microbubble of the first component, different examples are demonstrated in WO2015/047103, Example 5, and Tables 9 and 10, wherein various microbubble formulations with different excipients have been tested. The results demonstrate that the ACT concept used in the current invention is applicable to a wide variety of microbubble formulations, also with regards to the composition of the stabilizing membrane.

The microbubble size of the dispersed gas component should preferably be less than 7 μm, more preferably less than 5 μm and most preferably less than 3 μm in order to facilitate unimpeded passage through the pulmonary system, even when in a microbubble/microdroplet cluster.

The Second Component of the Cluster Composition:

The second component comprises a microdroplet comprising an oil phase and a second stabilizer to stabilize said microdroplet, where the oil comprises a diffusible component. This diffusible component is capable of diffusing into the gas microbubble of the first component so as to at least transiently increase the size thereof. For the second component the "diffusible component" is suitably a gas/vapour, volatile liquid, volatile solid or precursor thereof capable of gas generation, e.g. upon administration, the principal requirement being that the component should either have or be capable of generating a sufficient gas or vapour pressure in vivo (e.g. at least 50 torr and preferably greater than 100 torr) so as to be capable of promoting inward diffusion of gas or vapour molecules into the dispersed gas. The 'diffusible component' is preferably formulated as an emulsion (i.e. a stabilized suspension) of microdroplets in an appropriate aqueous medium, since in such systems the vapour pressure in the aqueous phase of the diffusible component will be substantially equal to that of pure component material, even in very dilute emulsions.

The diffusible component in such microdroplets is advantageously a liquid at processing and storage temperature, which may for example be as low as −10° C. if the aqueous phase contains appropriate antifreeze material, while being a gas or exhibiting a substantial vapour pressure at body temperature. Appropriate compounds may, for example, be selected from the various lists of emulsifiable low boiling liquids given in the patent applications WO-A-9416379 or WO2015/047103, the contents of which are incorporated herein by reference. Specific examples of emulsifiable diffusible components include aliphatic ethers such as diethyl ether; polycyclic oils or alcohols such as menthol, camphor or eucalyptol; heterocyclic compounds such as furan or dioxane; aliphatic hydrocarbons, which may be saturated or unsaturated and straight chained or branched, e.g. as in n-butane, n-pentane, 2-methylpropane, 2-methylbutane, 2,2-dimethylpropane, 2,2-dimethylbutane, 2,3-dimethylbutane, 1-butene, 2-butene, 2-methylpropene, 1,2-butadiene, 1,3-butadiene, 2-methyl-1-butene, 2-methyl-2-butene, isoprene, 1-pentene, 1,3-pentadiene, 1,4-pentadiene, butenyne, 1-butyne, 2-butyne or 1,3-butadiyne; cycloaliphatic hydrocarbons such as cyclobutane, cyclobutene, methylcyclopropane or cyclopentane; and halogenated low molecular weight hydrocarbons, e.g. containing up to 7 carbon atoms. Representative halogenated hydrocarbons include dichloromethane, methyl bromide, 1,2-dichloroethylene, 1,1-dichloroethane, 1-bromoethylene, 1-chloroethylene, ethyl bromide, ethyl chloride, 1-chloropropene, 3-chloropropene, 1-chloropropane, 2-chloropropane and t-butyl chloride. Advantageously at least some of the halogen atoms are fluorine atoms, for example as in dichlorofluoromethane, trichlorofluoromethane, 1,2-dichloro-1,2-difluoroethane, 1,2-dichloro-1,1,2,2-tetrafluoroethane, 1,1,2-trichloro-1,2,2-trifluoroethane, 2-bromo-2-chloro-1,1,1-trifluoroethane, 2-chloro-1,1,2-trifluoroethyl difluoromethyl ether, 1-chloro-2,2,2-trifluoroethyl difluoromethyl ether, partially fluorinated alkanes (e.g. pentafluoropropanes such as 1H,1H,3H-pentafluoropropane, hexafluorobutanes, nonafluorobutanes such as 2H-nonafluoro-t-butane, and decafluoropentanes such as 2H,3H-decafluoropentane), partially fluorinated alkenes (e.g. heptafluoropentenes such as 1H,1H,2H-heptafluoropent-1-ene, and nonafluorohexenes such as 1H,1H,2H-nonafluorohex-1-ene), fluorinated ethers (e.g. 2,2,3,3,3-pentafluoropropyl methyl ether or 2,2,3,3,3-pentafluoropropyl difluoromethyl ether) and, more preferably, perfluorocarbons. Examples of perfluorocarbons include perfluoroalkanes such as perfluorobutanes, perfluoropentanes, perfluorohexanes (e.g. perfluoro-2-methylpentane), perfluoroheptanes, perfluorooctanes, perfluorononanes and perfluorodecanes; perfluorocycloalkanes such as perfluorocyclobutane, perfluorodimethyl-cyclobutanes, perfluorocyclopentane and perfluoromethyl-cyclopentane; perfluoroalkenes such as perfluorobutenes (e.g. perfluorobut-2-ene or perfluorobuta-1,3-diene), perfluoropentenes (e.g. perfluoropent-1-ene) and perfluorohexenes (e.g. perfluoro-2-methylpent-2-ene or perfluoro-4-methylpent-2-ene); perfluorocycloalkenes such as perfluorocyclopentene or perfluoro-cyclopentadiene; and perfluorinated alcohols such as perfluoro-t-butanol. Hence, the oil (the diffusible component) of the second component may be selected from the group of aliphatic ethers, heterocyclic compounds, aliphatic hydrocarbons, halogenated low molecular weight hydrocarbons and perfluorocarbons. In one embodiment, the oil phase of the second component comprises a perfluorocarbon.

Particularly useful in the current invention are diffusible components with an aqueous solubility below $1 \cdot 10^{-4}$ M, more preferably below $1 \cdot 10^{-5}$ M. It should be noted, however, that if a mixture of diffusible components and/or co-solvents are used, a substantial fraction of the mixture may contain compounds with a higher water solubility. Based on the water solubility, examples of suitable oils (diffusible components) are: perfluorodimethylcyclobutane, perfluoromethylcylopentane, 2-(trifluoromethyl)perfluoropentane and perfluorhexane.

It will be appreciated that mixtures of two or more diffusible components may if desired be employed in accordance with the invention; references herein to "the diffusible component" are to be interpreted as including such mixtures.

The second component will also contain material in order to stabilize the microdroplet dispersion, in this text termed 'second stabilizer'. The second stabilizer may be the same as or different from any materials(s) used to stabilize the gas dispersion, e.g. a surfactant, such as a phospholipid, a polymer or a protein. The nature of any such material may significantly affect factors such as the rate of growth of the dispersed gas phase. In general, a wide range of surfactants may be useful as stabilizers, for example selected from the extensive lists given in EP-A-0727225, the contents of which are incorporated herein by reference. Representative examples of useful surfactants include fatty acids (e.g. straight chain saturated or unsaturated fatty acids, for example containing 10-20 carbon atoms) and carbohydrate and triglyceride esters thereof, phospholipids (e.g. lecithin), fluorine-containing phospholipids, proteins (e.g. albumins such as human serum albumin), polyethylene glycols, and polymer such as a block copolymer surfactants (e.g. polyoxyethylene-polyoxypropylene block copolymers such as Pluronics, extended polymers such as acyloxyacyl polyethylene glycols, for example polyethyleneglycol methyl ether 16-hexadecanoyloxy-hexadecanoate, e.g. wherein the polyethylene glycol moiety has a molecular weight of 2300, 5000 or 10000), and fluorine-containing surfactants (e.g. as marketed under the trade names Zonyl and Fluorad, or as described in WO-A-9639197, the contents of which are incorporated herein by reference). Particularly useful surfactants include phospholipids, and particularly phospholipids comprising molecules with overall neutral charge, e.g. distearoyl-sn-glycerol-phosphocholine (DSPC). For the second component, a range of different stabilizers may be used to stabilize the microdroplet. Further, a wide range of ionic, preferably cationic, substances may be used in order to facilitate a suitable surface charge.

It will be appreciated that, to facilitate attractive electrostatic interactions to achieve clustering between the microbubbles in the first component and the emulsion microdroplets in the second component, these should be of opposite surface charge. Hence, if the microbubbles of the first component are negatively charged, the microdroplets of the second component should be positively charged, or vice versa. In a preferred embodiment, the surface charge of the microbubbles of the first component is negative, and the surface charge of the microdroplets of the second component is positive. In order to facilitate a suitable surface charge for the oil microdroplets a cationic surfactant may be added to the stabilizing structure. A wide range of cationic substances may be used, for example at least somewhat hydrophobic and/or substantially water-insoluble compounds having a basic nitrogen atom, e.g. primary, secondary or tertiary amines and alkaloids. A particularly useful cationic surfactant is stearylamine. In one embodiment, the second stabilizer is a neutral phospholipid added a cationic surfactant such as a DSPC-membrane with stearylamine.

In one embodiment, the first stabilizer and the second stabilizer each independently comprises a phospholipid, a protein, a polymer, a polyethyleneglycol, a fatty acid, a positively charged surfactant, a negatively charged surfactant or mixtures thereof.

In one embodiment, the first component comprises a dispersed gas selected from the group of sulphur hexafluoride, perfluoropropane, perfluorobutane, perfluoropentane, perflurohexane, nitrogen and air or a mix thereof, stabilized by a first stabilizer selected from the group of phospholipids, proteins and polymers; the second component comprises a diffusible component selected from the group of perfluorocarbons, e.g. a perfluorocycloalkane, stabilized with a second stabilizer selected from the group of surfactants, e.g. including phospholipids, polymers and proteins. More specifically, either of the stabilizers are selected from phospholipids.

The first and second components are combined shortly before the intended use, to prepare the cluster composition, and for use in an appropriate time window. It will also be appreciated that the mixing of the first and second components can be achieved in various manners depended on the form of the components; e.g. mixing two fluid components, reconstitution of one component in dry powder form with one component in fluid form, mixing two components in dry form prior to reconstitution with fluid (e.g. water for injection or buffer solution). Also, it will be appreciated that other components may influence the ability of the microbubbles and microdroplets to form clusters upon mixing including, but not limited to; the level of surface charge of the microbubbles/microdroplets, the concentration of the microbubbles/microdroplets in the two components, the size of the microbubbles/microdroplets, the composition and concentration of ions in the liquid matrix, the pH, the composition and concentration of excipients (e.g. buffer or tonicity components) etc. (see WO2015/047103, Example 1). Such characteristics of the components and the composition may also influence the size and stability (both in-vitro and in-vivo) of the clusters generated and may be important factors influencing biological attributes (e.g. efficacy and safety profile). It is also appreciated that not all of the microbubbles/microdroplets in the cluster composition may be present in clustered form, but that a substantial fraction of the microbubbles and/or microdroplets may be present together in a free (non-clustered) form together with a population of microbubble/microdroplet clusters. In addition, the way the two components are mixed may influence these aspects, including, but not limited to; shear stress applied during homogenization (e.g. soft manual homogenization or strong mechanical homogenization) and time range for homogenization. The cluster composition is to be administered to the subject during a time window wherein the characteristics of the clusters are substantially unchanged, such as within 5 hours, such as within 3 hours, from combining the two components. In-use stability studies of the applicant show that the clusters display stable characteristics for at least 3 hours, please see Example 1.

The microdroplet size of the dispersed diffusible component in emulsions intended for intravenous injection should preferably be less than 7 μm, more preferably less than 5 μm, most preferably less than 3 μm, and greater than 0.5 μm, more preferably greater than 1 μm in order to facilitate unimpeded passage through the pulmonary system, but still retain a volume that is sufficient for activated bubble retention in the microvasculature.

Growth of the dispersed gas phase in vivo may, for example, be accompanied by expansion of any encapsulating material (where this has sufficient flexibility) and/or by abstraction of excess surfactant from the administered material to the growing gas-liquid interfaces. It is also possible, however, that stretching of the encapsulating material and/or interaction of the material with ultrasound may substantially increase its porosity. Whereas such disruption of encapsulating material has hitherto in many cases been found to lead to rapid loss of echogenicity through outward diffusion and dissolution of the gas thereby exposed, we have found that when using compositions in accordance with the present invention, the exposed gas exhibits substantial stability. Whilst not wishing to be bound by theoretical calculations, we believe that the exposed gas, e.g. in the form of liberated microbubbles, may be stabilized, e.g. against collapse of the microbubbles, by a supersaturated environment generated by the diffusible component, which provides an inward pressure gradient to counteract the outward diffusive tendency of the microbubble gas. The exposed gas surface, by virtue of the substantial absence of encapsulating material, may cause the activated bubbles to exhibit exceptionally favourable acoustic properties as evidenced by high backscatter and low energy absorption (e.g. as expressed by high backscatter: attenuation ratios) at typical diagnostic imaging frequencies; this echogenic effect may continue for a significant period, even during continuing ultrasound insonation.

In Vivo Activation and Enhancement:

The invention provides a pharmaceutical composition as disclosed above for use in an Acoustic Cluster Therapy (ACT) treatment comprising the steps of:

(i) administering the pharmaceutical composition to a mammalian subject with pancreatic cancer; wherein at least one therapeutic agent is pre-, and/or co- and/or post administered separate to the cluster composition;

(ii) optionally imaging the clusters of said pharmaceutical composition using ultrasound imaging to identify the region of interest for treatment within said subject;

(iii) activating a phase shift of the diffusible component of the second component of the cluster composition from step (i) by ultrasound insonation of a region of interest within said subject, (iv) facilitating extravasation of the therapeutic agents administered in step (i) by further ultrasound irradiation.

In the method of the invention, for treatment or delivery, the method comprises the above-mentioned steps.

The acoustic resonance of the microbubble component of the clusters is within the diagnostic frequency range (1-10 MHz). When the cluster composition has been administered to the subject, activation of the clusters is readily obtained with standard diagnostic ultrasound imaging pulses used for example in conventional medical ultrasound abdominal and cardiac applications, at mid-range to low mechanical indices, i.e. an MI below 1.9 and preferably below 0.7 and more preferably below 0.4, but above 0.1. Activation of the clusters to phase shift to produce larger (10 μm or more in diameter) phase shift bubbles can be achieved with a clinical imaging system to within millimetre spatial resolution by employing imaging pulses. Upon activation, the oil in the microdroplet vaporises and the resulting large, activated bubble, transiently deposits in the microvasculature. Further application of low frequency ultrasound after activation and deposition, facilitates enhancement of delivery mechanisms by effectively overcoming biological barriers to increase the efficiency of drug delivery to the cancerous pancreatic tissue. These mechanisms may include the process of sonoporation i.e. a process where insonation, and ensuing volume oscillation, of microbubbles in the vascular compartment increases the permeability of the vascular barrier. In other words, the ACT procedure increases the permeability of the endothelial wall and hence enhances the extravasation, distribution and cellular uptake of the therapeutic drug. Other mechanisms, such as generation of cellular signalling for enhanced therapeutic effect, mechanical breaking down of interstitial structures that enhances drug penetration etc. may also be induced.

The clusters are not activated at low MI (below the cluster activation threshold of approx. 0.1) allowing standard medical ultrasound contrast agent imaging to be performed, for example to identify tumour micro vascular pathology without activation of the clusters. Hence, in one embodiment the method includes a step of using low MI contrast agent imaging modes (MI<0.15) to image the microbubble component, i.e. the dispersed gas, without activation of the clusters, to identify the pathological location for treatment. Hence, as the clusters are not activated at low MI (below the activation threshold) standard medical ultrasound contrast agent imaging may be performed, prior to the activation step, for example to identify tumour microvascular pathology. Activation under medical ultrasound imaging control using the imaging pulses allows spatially targeted activation of the clusters in the tissue region being interrogated by the ultrasound field. After activation, the large phase shift bubbles produced are temporarily trapped in the microvasculature of the pancreas due to their size. The resulting large phase shift bubbles are approximately 1000 times the volume of the emulsion microdroplet vaporised (a 20 μm bubble diameter from a 2 μm diameter oil microdroplet). The scattering cross sections of these large phase shift bubbles are orders of magnitude greater than the scattering cross sections of the micron sized microbubbles comprised in the clusters before activation. As a result, the large phase shift bubbles produce copious backscatter signal and are readily imaged in fundamental imaging mode with diagnostic imaging systems. The mechanical resonance frequencies of the large phase shift bubbles are also an order of magnitude lower (1 MHz or less) than the resonance frequencies of the microbubbles comprised in the clusters before activation. Application of acoustic fields commensurate with the resonance frequencies of the larger phase shift bubbles produces relatively large radial oscillations at MI's within the medical diagnostic range. Thus, low frequency ultrasound, in the range of 0.05 to 2 MHz, preferably 0.1 to 1.5 MHz, more preferably 0.1 to 1.0 MHz, even more preferably 0.2 to 1 MHz, most preferably 0.4 to 0.6 MHz, and particularly 0.33-0.65 MHz can be applied to produce the bio-effect mechanisms that enhance the uptake of the administered drug, and hence facilitates extravasation. It has been found that after activation in-vivo, the majority of the activated bubbles are contained within 10 to 20 μm in diameter. The Minnaert resonance frequency of free microbubbles of this size is from 0.65 to 0.33 MHz. Hence, a most preferred frequency range for the low frequency enhancement step is 0.33-0.65 MHz. Exploiting the resonance effects of the activated bubbles allows better control of initiation of these bio-effects at lower acoustic intensities and at lower frequencies than possible with other technologies. Coupled with the fact that the large phase shift bubbles are activated and deposited in the tissue microvasculature under imaging control (allowing spatial targeting of the large activated bubbles in tissue), and their prolonged residence time, allows more efficient and controlled implementation of the drug delivery mechanisms.

It is envisioned that the ACT concept for drug delivery to the pancreas and treatment of PDAC, i.e. the composition for use of the invention, is a concept that applies for a broad combination of components (first and second) components, and also for a wide range of therapeutic agents.

Therapeutic Agent:

The therapeutic agent, also called "the drug", to be delivered to the subject is selected from the group of chemotherapeutic agents and immunotherapeutic agents. This is administered as a separate composition to the cluster composition. Examples of the therapeutic agent classes, and specific agents, useful in the claimed invention include, but are not limited to, the following:

Alkylation Agents

Nitrogen Mustards: Mechlorethamine Hydrochloride (Mustargen)

Nitrosoureas: Carmustine (BiCNU), Streptozocin (Zanosar), Lomustine (CeeNU)

Tetrazines: Dacarbazine (DITC-Dome), Temozolomide (Temodar)

Aziridines: Thiotepa (Thioplex), Mitomycin (Mutamycin), Aziridinylbenzoquinone (AZQ)

Cisplatins: Cisplatin (Platinol), Carboplatin (Paraplatin), Oxaliplatin (Eloxatin)

Antimetabolites

Anti-folates: Methotrexate (Otrexup, Rasuvo, Trexall), Pemetrexed (Altima)

Fluoropyrimidines: Fluorouracil (Adrucil), Capecitabine (Xeloda)

Deoxynucleotide analogues: Cytarabine (Cytosar-U), Decitabine (Dacogen), Azacitidine (Vidaza), Gemcitabine (Gemzar), Fludarabine (Fludara), Nelarabine (Arranon), Pentostatin (Nipent)

Thiopurines: Thioguanine (Tabloid), Mercaptopurine (Purinethol, Purixan)

Anti-Microtubule

Vinca alkaloids: Vinorelbine (Navelbine), Vinicristine (Oncovin, Vincasar Pfs), Vindesine (Eldisine), Vinflunine (Javlor)

Taxanes: Paclitaxel or nab-Paclitaxel (Onxol, Abraxane), Cabazitaxel (Jevtana), Docetaxel (Docetaxel, Docefrez)

Podophyllotoxin: Etoposide (Eposin, Etoposide), Teniposide (Vumon)

Topoisomerase Inhibitors

Topoisomerase I: Irinotecan (Onivyde), Topotecan (Act Topotecan, Hycamtin)

Topoisomerase II: Doxorubicine (Adriamycin, Caelyx), Mitoxantrone (Novantrone), Teniposide (Vumon), Novobiocin (Novobiocin Sodium), Merbarone, Aclarubicin Cytotoxic Antibiotics Anthracyclines: Doxorubicine (Adriamycin, Caelyx), Daunorubicin (Cerubidine, DaunoXome), Epirubicin (Ellence), Idarubicin (Idamycin), Bleomycin (Blenoxane), Mitomycin (Mitosol, Mutamycin)

Immunotherapies

CAR-T cell therapy: Sipuleucel-T (Provenge), Tisangenlecleucel (Kymriah), Axicabtagene ciloleucel (Yescarta)

Antibody therapies: Alemtuzumab (Campath CD52), Atezolizumab (Tecentriq PD-L1), Ipilimumab (Yervoy CTLA4), Pembrolizumab (Keytruda PD-1), Durvalumab (Imfinizi IgG1k)

Oncolytic virus: Talimogene laherparepvec (OncoVEX GM-CSF/T-vecIMLYGIC) Ad2/5 dl1520 (Onyx-015), GLV-1 h68 (GL-ONC1), CV706

Cancer Vaccines: Oncophage, Sipuleucel-T (Provenge)

Cytokine Therapy

Interferon: IFNα (Infergen), IFNβ (Actimmune)

Interleukin: No commercial product, In trials.

In one embodiment, the therapeutic agent is selected from the group of Alkylating agents, Antimetabolites, Anti-microtubules, Topoisomerase inhibitors, Cytotoxic antibiotics, Immunotherapeutic agents and Cytokine therapeutic agents.

In one embodiment, the therapeutic agent is formulated in a vehicle, such as included in the form of liposomes, conjugates, nanoparticles or microspheres, used as vehicles for the therapeutic agent. Hence, the therapeutic agent may be part of a larger drug construct such as nano-drugs, e.g. in liposomal or particulate formulations, or as monoclonal antibodies. Hence, in one embodiment, the therapeutic agent is formulated in closed lipid spheres, such as including the therapeutic agent in a liposomal formulation.

As shown in Example 2, the inventors have evaluated the synergistic effects of combining ACT with the large construct, nano-drug nab-paclitaxel (paclitaxel bound to albumin protein in nano-particles) and the nano-drug liposomal irinotecan. As noted, the ACT concept may be particularly useful for combination with such larger drug molecules or constructs, also as indicated by Example 3.

Examples of suitable approved therapeutic agents, wherein these are formulated in the form of a vehicle are;
   the liposomal chemotherapy drug Doxil™, wherein doxorubicin is encapsulated in liposomes;
   the liposomal chemotherapy drug Onivyde®, wherein irinotecan is encapsulated in liposomes; and
   the paclitaxel albumin-bound particle suspension Abraxane®.

Further, combination regimes between one or several chemotherapeutic agents with one or several immune therapeutic agents are preferred. Further, newer generation of liposomes containing two anticancer drugs with a single liposome, and immunoliposomes that comprise an antibody conjugated to a liposome, are encompassed by the invention.

In a preferred embodiment, the therapeutic agent is selected from a group of large molecules (e.g. proteins or antibodies) or nano-construct drugs which include, but is not limited to, the combination of nab-paclitaxel/gemcitabine, liposomal irinotecan, liposomal doxorubicin and monoclonal antibodies.

In a second preferred embodiment, the therapeutic agent is selected from a group of immunotherapeutic agents such as oncolytic viruses which include, but is not limited to, adenovirus, reovirus, measles, herpes simplex, Newcastle disease virus, and vaccinia. The viruses can cause cancer cells to "burst", killing the cancer cells and releasing cancer antigens. These antigens can then stimulate immune responses that can seek out and eliminate any remaining tumour cells nearby and potentially anywhere else in the body.

In one embodiment, the therapeutic agent comprises nab-paclitaxel (Abraxane) in combination with gemcitabine. In another embodiment, the therapeutic agent is liposomal irinotecan (Onivyde®).

In yet another embodiment, several therapeutic agents are administered as a combination regimen. Examples of suitable combination regimens include the combination regimen comprising leucovorin, fluorouracil, irinotecan and oxaliplatin (FOLFIRINOX), a combination regimen comprising leucovorin, fluorouracil and irinotecan (FOLFIRI), and a combination regimen comprising leucovorin, fluorouracil and oxaliplatin (FOLFOX).

In yet another embodiment, the therapeutic agent is an immunotherapeutic agent, such as a check-point inhibitor, such as an anti-PD1, anti-CTLA4 or anti-PDL1 checkpoint inhibitor.

In one embodiment of the invention, the method comprises treatment with at least one chemotherapeutic agent, combined with treating the subject with immunotherapy.

Disclaimer: In one embodiment, the therapeutic agent is not paclitaxel, i.e. as the free non-albumin-bound form. In one embodiment, the therapeutic agent is not a combination of gemcitabine with nab-paclitaxel.

In addition to the separately administered therapeutic agent, in one embodiment, the second component of the cluster composition comprises a further therapeutic agent included in the microdroplet.

Administration Routes:

The cluster composition is administered to said mammalian subject parenterally, preferably intravenously. The route of administration might also be selected from the intraarterial, intramuscular, intraperitoneal, intratumoral or subcutaneous administration. For administration to the subject, the therapeutic agent is pre-, and/or co- and/or post administered separate to the cluster composition as a separate composition. The therapeutic agent is administered according to the respective approved Summary of Product Characteristics. Typically, the route is selected from the group comprising, but not limited to, intravenous, intraperitoneal, intratumoral and intramuscular administration. The two compositions, i.e. the cluster composition (a) and the therapeutic agent composition (b) may hence be administered via the same or via different routes of administration.

Treatment Schedules:

It will be appreciated that the composition for use, the method for treatment, and/or the method for delivery of drugs, of the invention, may e.g. be employed as part of a multi-drug treatment regimen. In one embodiment, the pharmaceutical composition for use according to the invention, includes the use of more than one therapeutic agent. Such chemotherapeutic combination regimen may e.g. comprise leucovorin, fluorouracil, irinotecan (FOLFIRI).

Furthermore, in one embodiment, several ACT treatments can be performed during the period of administering the therapeutic agents, e.g. as exemplified in FIG. 5 and FIG. 6. In one embodiment, the method of treatment includes 1 to 5, such as 2 to 4, ACT treatments. The "ACT treatment" or "ACT procedure" include at least the administration of a cluster composition, the activation of the clusters by regular medical imaging US insonation and the following, low frequency US insonation to induce enhanced uptake. The FIG. 5 and FIG. 6 provide examples of treatment schedules.

FIG. 5 shows a graph of ACT treatments performed during treatment with the following chemotherapy combination regimen FOLFOX:

2 hours infusion of oxaliplatin and lecovorin followed by bolus injection of fluorouracil (5-FU) and 48 hours infusion of 5-FU. The ACT procedure is applied three times during the chemotherapy administration, as indicated by grey ACT® sonoporation bars.

Panel A of the FIG. 5: each ACT procedure consists of
a.: injection of the cluster composition,
b.: activation of clusters with 60 second of regular medical imaging ultrasound insonation, and
c.: enhancement step with 5 minutes of 400 to 600 kHz ultrasound insonation.

Panel B of FIG. 5: y-axis showing plasma concentration of administered chemotherapeutics in percent of peak and x-axis showing time in minutes. In this example three ACT procedures are performed at approximately 50 minutes, 80 minutes and 110 minutes in order to cover all three drugs. In FIG. 6, similar schematics are shown for the Standard of Care combination regimen for treatment of PDAC; gemcitabine and nab-paclitaxel.

The inventors have found that it is beneficial to repeat the ACT procedure, rather than applying a single ACT procedure for each administration of therapeutic agent. Using US imaging during activation of ACT, the inventors have observed a notable effect in deposition of ACT bubbles in tumours. A strong variance in the deposition pattern from injection to injection in the same animal was observed; the density of deposited ACT bubbles differed between various segments of the tumour, and this pattern changed between injections. Although not fully elucidated, it is hypothesised that these effects are due to a temporal variation in perfusion for various tumour segments. Based on these observations, in order to reach as much of the tumour volume as possible, in the examples, the inventors have applied the ACT procedure three consecutive times, back to back. This also points to the benefit of applying several ACT procedures during clinical use, as noted above for the FOLFOX and NAB/GEM regimens.

Hence, in one embodiment, more than one therapeutic agent, such as 1 to 5 therapeutic agents, are administered simultaneously or sequentially over a certain time span, such as over up to 3 hours, wherein at least one, such as 1 to 5, ACT treatments are performed during the same period.

In one embodiment, the following ACT procedure is provided; The administration, such as an intravenous administration, of a cluster composition is followed by local US insonation of the tumour with regular medical imaging US (activation), followed by low frequency US insonation to induce enhanced uptake (facilitating extravasation), and these steps are performed 2-5 consecutive times, such as 3 consecutive times. Hence, the steps (i) to (iv) of the ACT treatment are repeated one to four times. This is performed in conjunction with administration of therapeutic agents. The activation, i.e. the initial US insonation, should start immediately after each administration of the cluster composition, such as within one minute, and lasts for e.g. 30-120 seconds. The insonation with low frequency ultrasound follows the activation step and should typically last for 3 to 10 minutes, such as for about 5 minutes. There is preferably an immediate start of step (iv) after step (iii). A dual frequency transducer may beneficially be used in the treatment, for both the activation step and the enhancement step. By using such, the switch from the activation insonation in step (iii) to the enhancement insonation in step (iv) can be made without any delay. Application of the enhancement field immediately after activation may be important for the resulting therapeutic benefit. In this respect it would be beneficial to apply both the activation and the enhancement insonation using a broad band or dual frequency US transducer. I.e. a transducer capable of delivering sufficient US pressure (i.e. MI) over all frequencies required by the stated preferred ranges. E.g. a transducer capable of delivering MIs of up to 0.4 at both 1 to 10 MHz and at 400 to 600 kHz.

In another embodiment, the multidrug regimen comprises an anti-PD1, anti-PDL1 or CTLA4 monoclonal antibody and a chemotherapeutic agent, e.g. pembrolizumab+cisplatin plus oxaliplatin (5-FU) or capecitabine. Hence, several therapeutic drugs can be used, and several ACT procedures can be applied during the treatment regimen. In a preferred embodiment, the ACT procedure is performed when the active therapeutic molecule displays maximum or close to maximum concentration in the blood after administration. Hence, the timing of the ACT treatment(s) may vary dependent upon the pharmacokinetics of the therapeutic agent.

The therapeutic agent(s) are pre-, and/or co- and/or post administered separate to the cluster composition. In a preferred embodiment, a therapeutic agent is administered after the administration of one of the at least one cluster compositions. Surprisingly, in Example 2 it was found that performing the ACT treatment, i.e. the administration and insonation of the clusters, before administration of the therapeutic agent showed similar effect size as if the ACT treatment was initiated after administration of the therapeutic agent (i.e. when the therapeutic agent is in the blood stream). This finding indicates that the bio-mechanical effects induced by ACT, i.e. the increased permeability of the vascular barrier, last for some time after the US procedure has terminated. This may be beneficial in clinical practice, as the ACT treatment may be performed prior to starting the therapeutic administration and treatment. Hence, in one embodiment, a therapeutic agent is administered after the cluster composition has been administered and US insonated in-vivo. In another embodiment, the cluster composition is administered either immediately prior to or immediately after administration of therapeutic agent(s), such as chemotherapies.

Results:

The inventors have found that applying the ACT concept in treatment of PDAC in combination with treatment with at least one of a chemotherapeutic agent and/or an immunotherapeutic agent, i.e. as provided according to the invention, provides a remarkable increase in the therapeutic effect, when compared to using the therapeutic agents alone, i.e. without the use of the claimed method or composition, and at the same dose. The pharmaceutical composition for use, and the method of treatment, result in improved uptake of the therapeutic agent, e.g. as a result of the facilitated extravasation of the therapeutic agent(s) and the therapeutic efficacy is remarkedly enhanced. The treatment provides a significant inhibition of tumour growth, induced tumour shrinkage, and hence a reduction in tumour volume. As an overall result, the method may provide an improvement in survival time. Using the method of the invention, a reduction of the PDAC tumour volume of more than 50%, such as more than 75%, such as 90%, may be achieved. As shown in Examples 2 and 3, an 85% or even a 90% reduction in tumour volume was achieved using the method of the invention, compared to treatment with drugs alone, at day 50 after the initial drug dosing. Further, as shown in Example 2, even complete remission can be achieved, and hence there is a significant increase in the fraction of complete responders, compared to treating without ACT. Using the method of the invention, the fraction of treated subjects for which complete remission is seen, e.g. at day 120 after initial drug dosing, is at least 40%, such as at least 50%, or even at least 60%. It should be noted that these effect levels are as observed in pre-clinical studies in mice and that effect levels in humans may be less. A further benefit of the method, is that the dose of the therapeutic agent may be reduced, compared to the normally used dose, resulting in reduced systemic side effects whilst still keeping or improving on the therapeutic effect. In Example 3, similar synergistic effects with combination with ACT were shown with the immunotherapeutic agent oncolytic reo-virus.

In one embodiment, the pharmaceutical composition of the invention is for use in delivery of therapeutic agents to the pancreas, particularly to subjects diagnosed with PDAC. The composition for use, and using the ACT technology, provides a site-specific delivery of the therapeutic agent, to reach an effective local concentration of the therapeutic agent, and further provides an improved uptake of this at the region of interest.

Hence, in one embodiment, the invention provides a pharmaceutical composition for use in a method of delivering a therapeutic agent, wherein the method comprises the steps of:

(i) administering the pharmaceutical composition as defined in the first aspect to a mammalian subject with PDAC; wherein at least one therapeutic agent is pre-, and/or co- and/or post administered to the cluster composition, and before steps ii) to iii) or after any of steps ii) to iii);

(ii) optionally imaging the clusters of said pharmaceutical composition using ultrasound imaging to identify the region of interest for treatment within said subject;

(iii) activating a phase shift of the diffusible component of the second component of the cluster composition from step (i) by ultrasound insonation of a region of interest within said subject, such that:

(a) the microbubbles of said clusters are enlarged by said diffusible component of step (iii) to give enlarged bubbles which are localised at said region of interest due to temporary deposition in the microcirculation at said region of interest by said enlarged bubbles; and (b) facilitating extravasation of the therapeutic agent(s) administered in step (i); and, (iv) facilitating further extravasation of the therapeutic agents administered in step (i) by further ultrasound insonation.

Equally, the invention provides a method of delivering at least one therapeutic agent to a mammalian subject, comprising the steps of:

(i) administering the pharmaceutical composition as defined in the first aspect to a mammalian subject;

(ii) optionally imaging the microbubbles of said pharmaceutical composition using ultrasound imaging to identify the region of interest for treatment within said subject;

(iii) activating a phase shift of the diffusible component of the second component of the cluster composition from step (i) by ultrasound irradiation of a region of interest within said subject, such that:

(a) the microbubbles of said clusters are enlarged by said diffusible component of step (iii) to give enlarged bubbles which are localised at said region of interest due to temporary blocking of the microcirculation at said region of interest by said enlarged bubbles; and (b) said activation of step (iii) facilitates extravasation of the therapeutic agent(s) administered in step (i); and, (iv) facilitating further extravasation of the therapeutic agents administered in step (i) by further ultrasound irradiation.

The methods and composition for use of the invention may be accompanied by diagnostic imaging, e.g. by doing ultrasound imaging including using the microbubbles of the clusters as contrast agents, as disclosed above, but may also be combined with other types of imaging studies, typically to diagnose and/or assess the outcome of the treatment. Such imaging may include abdominal computed tomography (CT), e.g. as an initial test to identify a pancreatic mass, or abdominal magnetic resonance imaging (MRI) with or without cholangiopancreatography (MRCP), abdominal ultrasonography (US), and endoscopic ultrasound (EUS) with or without endoscopic cholangiopancreatography (ERCP). EUS and ERCP are the most invasive of the above-mentioned tests but are the only studies among those listed that allow for a biopsy that may provide the exact diagnosis.

The embodiments and features described in the context of one aspect, e.g. for the aspect directed to the composition for use in therapy, also apply to the other aspects of the invention directed to the use in delivery or in the methods for treatment or delivery.

The following examples are provided to illustrate the invention in accordance with the principles of the invention, but are not to be construed as limiting in any way.

EXAMPLES

Reference is made to the applicant's application WO2015/047103, and particularly to the Examples of this, the contents of which are incorporated herein by reference, providing descriptions of analytical methodologies for characterisation of the clusters compositions, results from use of the clusters, etc.

In the following examples the 1st component is designated C1, the 2nd component is designated C2 and the cluster composition, i.e. the composition resulting from a combination of the 1st and 2nd components, is designated DP (drug product).

Example 1 provides descriptions of analytical methodologies for characterisation and quantitation of microbubble/microdroplet clusters in DP, and explains relevant responses and attributes including concentration, size and circularity. It also provides details on analytical methodology for characterisation and quantification of activated bubble size and concentration. In addition, data on cluster stability after preparation are presented, as is a comparison of characteristics for pre-mixed vs. co-injected DP. It also details engineering steps for controlled manipulations of cluster content and size in DP.

Example 1 further provides results from in-vivo studies elucidating effects of cluster characteristics on product efficacy as the ability to deposit large, activated bubbles in the microcirculation. It further analyses these data and concludes that clusters with a mean size between 3 to 10 μm, defined by a circularity of less than 0.9, are contributing to the efficacy of the cluster composition.

Example 1. Cluster Preparation, Analytical Tools and Basic Characteristics

The microbubble/microdroplet clusters formed upon combining C1 and C2, i.e. present in DP, are crucial to the critical quality attributes of the composition, i.e. its functionality for delivery of drugs. Hence, analytical methodology to characterize and control the clusters formed with regards to concentration and size, is an imperative tool to assess the current invention as well as for medicinal Quality Control (QC). We have identified three different analytical tools that can be applied for this purpose; Coulter counting, Flow Particle Image Analysis (FPIA) and Microscopy/Image analysis.

In addition to these techniques, applied for characterization of the clusters in the cluster composition, analytical methodology has been developed to study the activation of the clusters in vitro, i.e. the generation of large, activated bubbles upon ultrasound irradiation. This methodology; "Sonometry" is detailed in E1-6 of WO2015/047103. Primary report responses from the Sonometry analysis are number and volume of activated bubbles and their size distribution, both vs. time after activation. Activation responses may also be explored by Microscopy/Image analysis as detailed in E1-5 of WO2015/047103.

Components and Compositions:

The 1st component (C1) in the compositions investigated in the included example consisted of per-fluorobutane (PFB) microbubbles stabilized by a hydrogenated egg phosphatidyl serine-sodium (HEPS-Na) membrane and embedded in lyophilized sucrose. HEPS-Na carries a negatively charged head group with an ensuing negative surface charge of the microbubbles. Each vial of C1 contains approximately 16 μL or $2 \cdot 10^9$ microbubbles, with a mean diameter of approximately 2.0 μm. The freeze-dried formulation displays long shelf life, more particularly 3 years, stored at ambient room temperature.

The 2nd component (C2) in the compositions investigated in this example consisted of perfluoromethyl-cyclopentane (pFMCP) microdroplets stabilized by a 1,2-Distearoyl-sn-glycerol-3-phosphocholine (DSPC) membrane with 3% mol/mol stearylamine (SA) added to provide a positive surface charge. The microdroplets in the C2 were dispersed in 5 mM TRIS buffer. The standard formulation of C2 investigated in these studies contains approximately 4 μL or $0.8 \cdot 10^9$ microdroplets per mL, with a mean diameter of approximately 1.8 μm. The 2nd component displays long shelf life, more particularly 18 months or more, stored refrigerated.

In some cases, to elucidate effects on cluster characteristics, a variety of formulation variables such as SA content, microdroplet size, microdroplet concentration, TRIS concentration and pH was varied in a controlled manner. In case such samples have been used, these aspects are detailed in the text.

The cluster composition (DP) was prepared aseptically by reconstituting a vial of C1 with 2 mL of C2 followed by 30 seconds of manual homogenisation. 2 mL was withdrawn from a vial of C2 using a sterile, single use syringe and needle. The content of the syringe was added through the stopper of a vial of C1 and the resulting DP was homogenised preparing the composition for administration.

As shown in WO2015/047103, the first and second components, i.e. the microbubble formulation and the microdroplet formulation, can be varied. E.g. as shown in tables 9 and 10 of WO2015/047103 both the gas and the stabilising membrane of the first component can be varied, to prepare clusters with suitable properties, expected to be useful in treatment according to the invention.

Stability of clusters in the cluster composition during analysis: The clusters in the DP are formed and held together by the electrostatic attraction between the microbubbles and the microdroplets. These forces are finite and the clusters may break up after formation through various routes/influences such as mechanical stress or thermal (Brownian) motion. For precise and accurate characterization, it is important that the clusters remain stable during the time of analysis. This stability has been investigated with all the methodologies described above. To evaluate stability, 3 to 5 analyses where repeated on a single DP sample covering a timespan of >5 minutes. No significant change in neither concentration nor size has been observed cross these replicates, proving that the microbubbles, microdroplets and clusters are stable for >5 minutes under the analytical conditions stated, i.e. after dilution in PBS or water and under continuous homogenization (stirring).

Formulation Aspects

A number of different formulation aspects can be explored for controlling the cluster content and size in the DP and for targeting optimal properties. Parameters that can be used to engineer cluster content and size distribution include, but are not limited to; the difference in surface charge between the microbubbles and the microdroplets e.g. SA %: the microdroplet size of C2: the pH: the concentration of TRIS in C2: and the concentration of microbubbles and microdroplets. In addition, chemical degradation of the components, e.g. during prolonged storage at high temperatures, may influence the ability of C1 and C2 to form clusters during preparation of the DP.

From in-vitro characterisation of 30 different compositions, as reported in WO2015/047103, several important correlations that elucidate the nature and characteristics of the system can be extracted. We found that the size of the clusters formed is also strongly connected to the Reactivity of the system. Only small clusters (i.e. 1-5 um) and medium sized clusters (i.e. 5-10 μm) are formed at relatively low levels of Reactivity (e.g. <20%). With increasing Reactivity, larger clusters start to form; at R >approx. 20%, 10-20 μm clusters start to form and at R >approx. 50%, 20-40 μm clusters start to form. When larger clusters form, it is at the expense of smaller and medium sized clusters; we found a clear optimum in content vs. Reactivity for cluster concentration 1-5 μm and 5 –10 μm. We found that formation of larger clusters (i.e. larger than 10 um, or larger than 20 um) is detrimental to the efficacy of the composition and that the clustering potential must be balanced accordingly.

Based on applicant's experiments, and the results shown in Tables 5 and 6 of WO2015/047103, the efficacy (linear enhancement in Grey Scale units (GS)) of the cluster composition is correlated with the cluster mean size and the concentration of clusters (million/ml). Grey Scale enhancement is the increase in brightness (contrast) observed by US imaging after administration and activation of the cluster composition in-vivo and is a measure of the amount of activated bubbles in the imaged tissue. The results reported there are from a multivariate, principal component analysis (PCA) of the contribution of clusters in various size classes to the linear enhancement in the ultrasound signal from dog myocardium (Grey Scale units) upon i.v. administration of the cluster composition and activation in the left ventricle, please see Example 2 of WO2015/047103. The PCA was performed on data for 30 samples detailed in Tables 5 and 6 of this. The results demonstrate that small and medium sized clusters (<10 μm) contribute significantly to the efficacy of the cluster composition whereas larger clusters (>10 μm) do not. These results and conclusion also apply for the current invention. The cluster size distribution is important, and the mean size should be in the range of 3-10 μm, and preferably 4-9 μm, more preferably 5-7 μm.

The cluster concentration and mean diameter of the cluster composition, prepared according to Example 1, was analysed and found to have a cluster concentration of about 40-44 million per mL and with a cluster mean diameter of about 5.8-6.2 μm, for several hours. The results are shown in Table 1 below and are consistent with the results of Table 6 of WO2015/047103. The data of Table 1 shows that the prepared cluster composition has an acceptable stability, and that an optimal size and concentration of clusters can be achieved.

TABLE 1

| Time (hours) | Cluster Concentration (millions/mL) | Cluster Mean Diameter (μm) |
|---|---|---|
| 0 h | 44 ± 2 | 6.0 ± 0.2 |
| 1 h | 43 ± 1 | 5.8 ± 0.2 |
| 2 h | 44 ± 5 | 6.2 ± 0.1 |
| 3 h | 40 ± 1 | 6.0 ± 0.2 |

Figure 1:
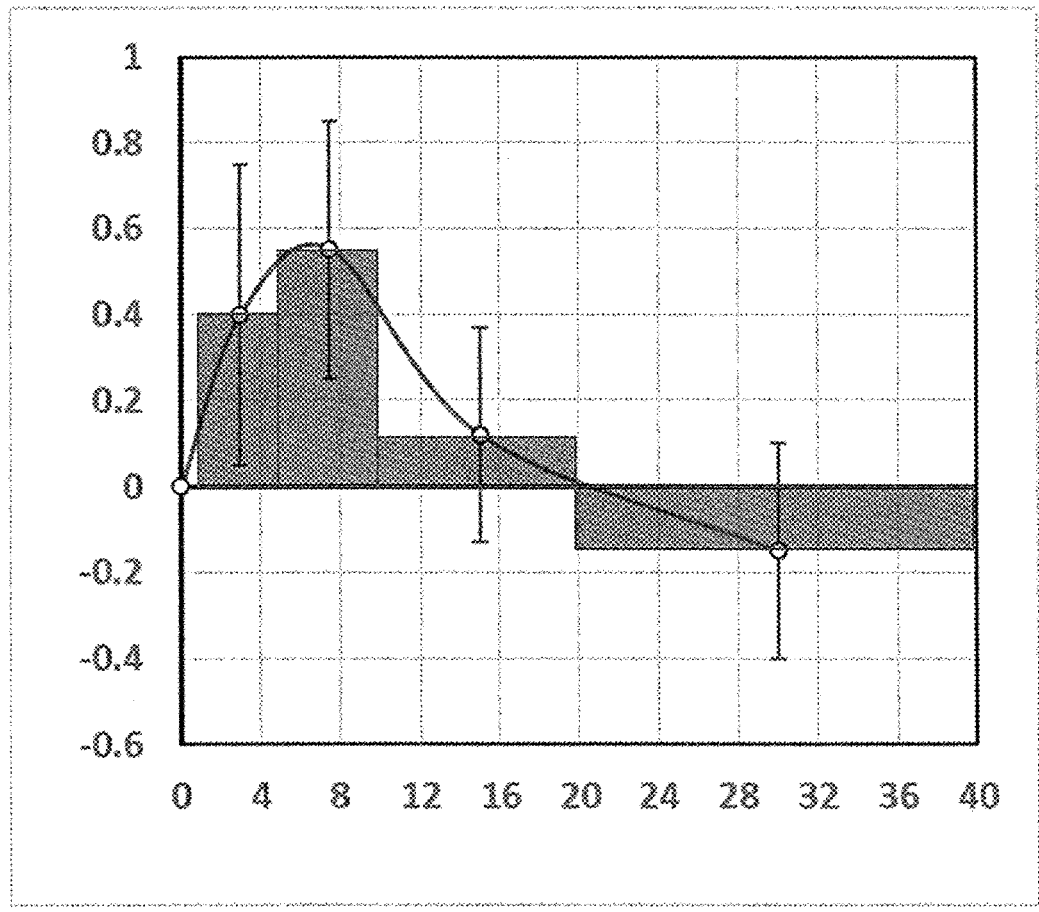
FIG. 1 provides a visualization of cluster size versus in-vivo product efficacy, wherein the Y-axis shows the calculated correlation coefficient for Grey Scale enhancement from US imaging (i.e. amount of bubbles deposited after activation) and the X-axis shows cluster diameter in μm.

The size of the clusters affects the efficacy. FIG. 1 shows a visualization of cluster size versus product efficacy, showing that clusters having a mean diameter in the range of 3 to 10 μm have an optimal efficacy. Hence, in FIG. 1 product efficacy vs. cluster diameter is provided. Y-axis shows correlation coefficient to Grey Scale enhancement from US imaging of dog myocardium after injection and activation of clusters in the left ventricle and reflects the amount of activated bubbles deposited. X-axis shows cluster diameter in μm. Grey boxes represent the different cluster size bins evaluated: 1 to 5 μm, 5 to 10 μm, 10 to 20 μm and 20 to 40 μm. Solid line represents the continuous function of efficacy vs. cluster diameter. Error bars are standard error. FIG. 1 is an alternative visualization of FIG. 12 (left side) of WO2015/047103 and is based on the data provided in Table 2 below.

TABLE 2

| Channel Group | Mean Channel Diameter | Efficacy Coefficient |
|---|---|---|
| 1 to 5 μm | 3 | 0.4 |
| 5 to 10 μm | 7.5 | 0.55 |
| 10 to 20 μm | 15 | 0.12 |
| 20 to 40 μm | 30 | −0.15 |

Applying the concept of the present invention, i.e. by preparing a cluster composition from C1 and C2 prior to administration, hence forming microbubble/microdroplet clusters, as opposed to co-injection of the two components as taught by WO/9953963, enable a >10-fold increase in efficacy. The formation of microbubble/microdroplet clusters upon combination of the 1 st component and 2nd component, and administering these pre-made clusters, is a pre-requisite for its intended functionality in-vivo. The cluster composition is to be administered to the subject during a time window wherein the characteristics of the clusters are substantially unchanged, such as within 3 hours from combining the two components.

Example 2. Therapeutic Effects in Patient-Derived Xenograft Mouse Models for PDAC—Acoustic Cluster Therapy with Chemotherapy Study Design: Acoustic Cluster Therapy (ACT) and compositions for use according to the invention (referred to as ACT) was investigated for therapeutic effect level with two different chemotherapy regimens.

Figure 2A:
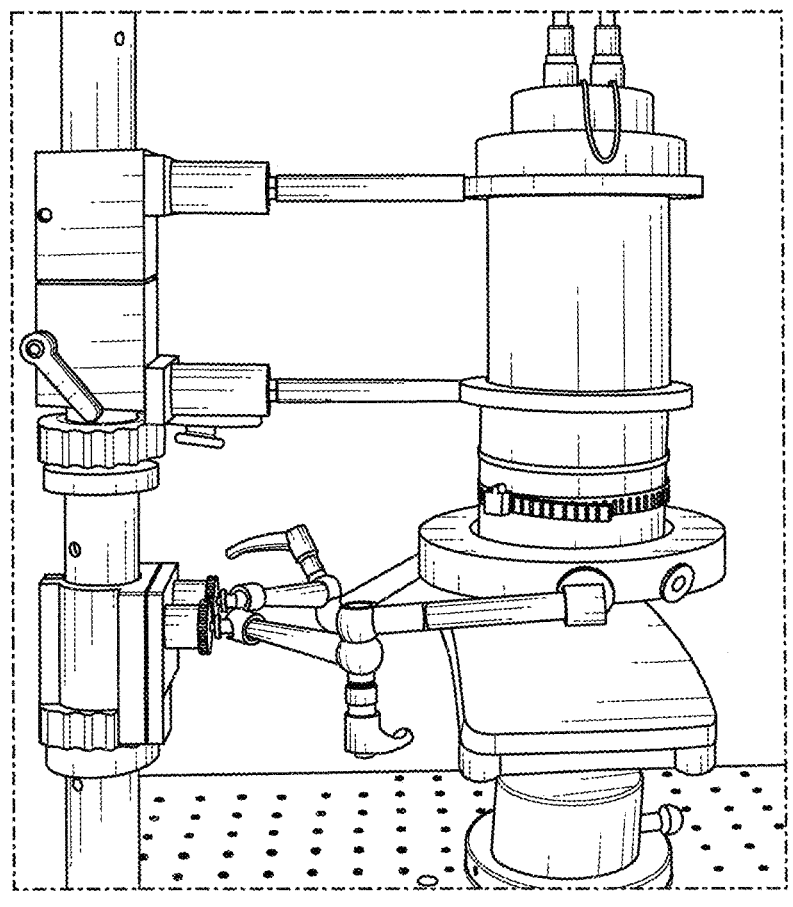
FIG. 2 provides A) a setup photograph and B) a set up sketch, of the apparatus used in the study of Example 2 and Example 3, for application of the ACT Sonoporation procedure comprising ultrasound activation and enhancement.
FIG. 2C provides an overview of the treatment schedule for the study of Example 2, wherein the therapeutic effects in treatment of patient-derived xenograft mouse models for PDAC are assessed.
Figure 2B:
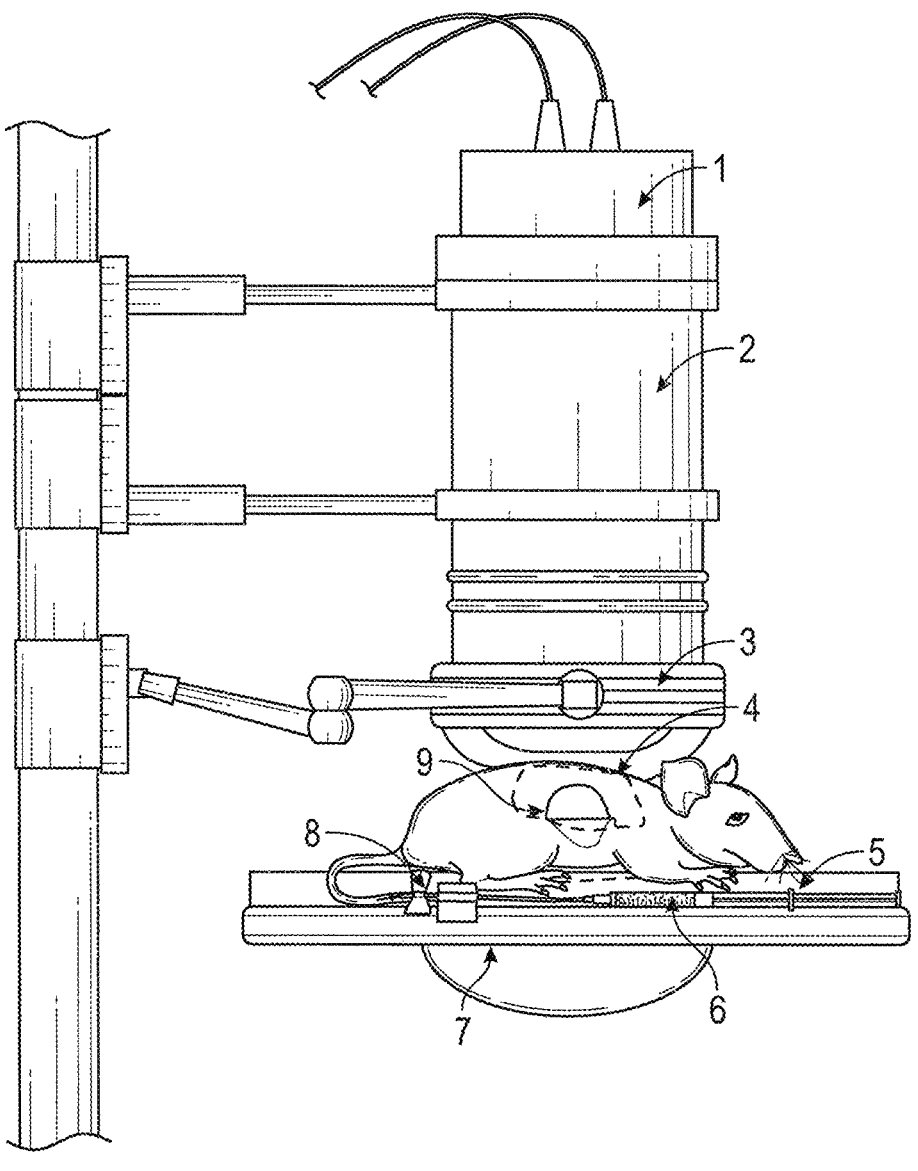

The following ACT procedure was used; intravenous administration of the cluster composition+local ultrasound (US) insonation of the tumour was performed 3 consecutive times either immediately prior to or immediately after administration of chemotherapies. The experimental set up (rig) and treatment schedules is depicted in FIG. 2, wherein FIG. 2A) provides a setup photograph and FIG. 2B) provides a set up sketch, of the apparatus used in the study, for ultrasound activation and enhancement. In FIG. 2B, the numbers denote the following: 1 is a dual frequency ultrasound transducer (2.7 MHz and 500 kHz output), 2 is an ultrasound waveguide, 3 is a water bath, 4 is ultrasound gel, 5 is an ultrasound absorber pad, 6 is an injection syringe with cluster composition, 7 is a VeVo imaging table, 8 is a catheter and 9 is a tumour.

Figure 2C:
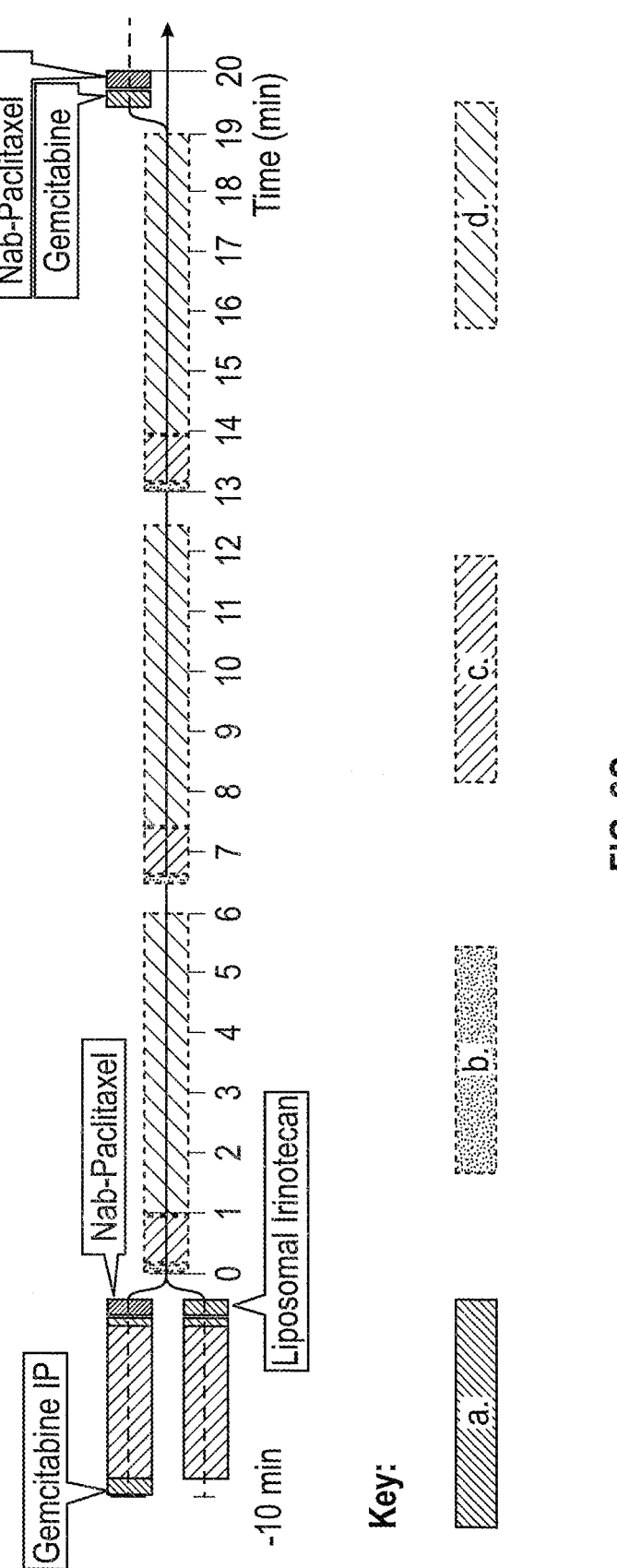

Further, FIG. 2C provides an overview of the treatment schedule, wherein the cluster composition was compounded by reconstituting one vial of Sonazoid™ (GE Healthcare) (Component 1 as outlined in Example 1) with 2 mL of a perfluoromethylcylopentane (PFMCP) emulsion, containing 6.8 mg PFMCP/mL. The PFMCP droplets were stabilized with distearoylphosphatidyl-choline with 3 M stearylamine (Component 2 as outlined in Example 1).

In FIG. 2C, the following denominations are used:
a.: mouse anaesthetized and catheterized,
b.: injection of cluster composition,
c.: 60 seconds of ultrasound activation at 2.7 MHz and
d.: 5 minutes of ultrasound enhancement at 500 kHz.
Injection of gemcitabine and nab-paclitaxel pre- or post-ACT treatment as indicated. Or, injection of liposomal irinotecan pre ACT treatment, as indicated.

Each ACT procedure comprised injection of 2 mL/kg of the cluster composition followed by US activation and enhancement steps.

PDAC patient-derived tumour xenografts were implanted subcutaneously into athymic nude mice which were enrolled into the treatment study when tumour size reached between $163 \pm 3$ (Standard Error of Mean) mm$^3$. The mice (7 to 10 mice/group, cf. Table 3) were treated with either chemotherapeutics alone or in combination with ACT. In addition, a saline+ACT control group was performed.

Two chemotherapeutic regimens were tested:
The nab-paclitaxel (NAB, 15 mg/kg, i.v., weekly×3) and gemcitabine (GEM, 60 mg/kg, i.p., weekly×3) combination (NAB/GEM), and
Liposomal irinotecan (ONI, 15 mg/kg, i.v., weekly×3).
Table 3 provides an overview of the treatment groups and the number of animals in each group.

Gemcitabine was administered intraperitoneal (Gemcitabine IP) and Nab-paclitaxel was administered intravenously (Nab-Paclitaxel IV) and liposomal irinotecan was administered intravenously (Liposomal irinotecan IV).

TABLE 3

Treatment groups investigated, number (n)
of animals in each group

| Groups | n | Treatment duration |
|---|---|---|
| 1. Saline followed by ACT | 10 | Weekly for |
| 2. NAB/GEM | 9 | three weeks |

TABLE 3-continued

Treatment groups investigated, number (n)
of animals in each group

| Groups | n | Treatment duration |
|---|---|---|
| 3. NAB/GEM followed by ACT | 10 | |
| 4. ACT followed by NAB/GEM | 7 | |
| 5. Liposomal irinotecane (ONI) | 9 | |
| 6. Liposomal irinotecan (ONI) followed by ACT | 9 | |

The Animals were monitored daily for body weight and tumour size via caliper measurement for 49 days after study start. At day 49, animals that showed progressive disease were culled whereas animals that showed significant remission (as defined by a tumour size <60 mm$^3$) were monitored for up 120 days. At 120 days, the fraction of complete responders in each group, defined as animals with no measurable remaining tumour mass, was determined. Tumour volume was normalized to 150 mm$^3$ at first treatment day (Day 0).

Results:
The results for average tumour volume and standard error of the mean (SEM) are stated in Table 4 and Table 5 below.

TABLE 4

Results for average tumour volume and standard error of the mean
(SEM) vs. time, of treatment groups administered ,
with liposomal irinotecan (ONI)
Saline control, and liposomal irinotecan plus ACT (ONI + ACT).

| Time Days | ONI Tumour volume (mm³) | SEM | Saline Tumour volume (mm³) | SEM | ONI + ACT Tumour volume (mm³) | SEM |
|---|---|---|---|---|---|---|
| 0 | 150.0 | 0.0 | 150.0 | 0.0 | 150.0 | 0.0 |
| 4 | 159.9 | 6.8 | 161.8 | 4.4 | 126.5 | 6.5 |
| 7 | 166.9 | 7.1 | 177.7 | 8.9 | 103.8 | 5.7 |
| 10 | 177.8 | 8.8 | 216.8 | 16.4 | 88.7 | 6.7 |
| 14 | 164.5 | 11.9 | 238.6 | 19.5 | 73.8 | 5.2 |
| 17 | 164.1 | 17.2 | 312.2 | 25.8 | 57.5 | 5.0 |
| 21 | 153.7 | 17.8 | 345.2 | 32.4 | 48.8 | 6.4 |
| 25 | 183.0 | 23.9 | 391.6 | 43.2 | 48.3 | 5.9 |
| 28 | 170.2 | 26.7 | 444.9 | 51.7 | 45.8 | 6.4 |
| 32 | 167.1 | 29.5 | 501.0 | 60.4 | 38.1 | 4.8 |
| 35 | 160.8 | 31.9 | 555.6 | 68.4 | 36.3 | 6.2 |
| 39 | 180.5 | 45.8 | 627.5 | 75.6 | 32.1 | 6.1 |
| 42 | 195.2 | 60.4 | 699.2 | 94.0 | 25.9 | 5.3 |
| 45 | 237.8 | 78.0 | 805.8 | 111.6 | 27.5 | 5.9 |
| 49 | 253.6 | 84.4 | 893.7 | 118.1 | 36.1 | 9.3 |

TABLE 5

Results for average tumour volume and standard error of the mean
(SEM) vs. time, of treatment groups administered with nab-paclitaxel/gemcitabine
(NAB/GEM), Saline control, and nab-paclitaxel/gemcitabine plus ACT prior to or
after administration of drug (ACT + NAB/GEM and NAB/GEM + ACT,
respectively).

| Time Days | NAB/GEM Tumour volume (mm³) | SEM | NAB/GEM + ACT Tumour volume (mm³) | SEM | Saline Tumour volume (mm³) | SEM | ACT + NAB/GEM Tumour volume (mm³) | SEM |
|---|---|---|---|---|---|---|---|---|
| 0 | 150.0 | 0.0 | 150.0 | 0.0 | 150.0 | 0.0 | 150.0 | 0.0 |
| 4 | 154.2 | 7.7 | 139.0 | 3.6 | 161.8 | 4.4 | 124.2 | 5.6 |
| 7 | 155.0 | 12.1 | 116.0 | 5.7 | 177.7 | 8.9 | 109.5 | 8.5 |
| 10 | 151.5 | 12.1 | 98.7 | 6.3 | 216.8 | 16.4 | 94.4 | 10.7 |

TABLE 5-continued

Results for average tumour volume and standard error of the mean
(SEM) vs. time, of treatment groups administered with nab-paclitaxel/gemcitabine
(NAB/GEM), Saline control, and nab-paclitaxel/gemcitabine plus ACT prior to or
after administration of drug (ACT + NAB/GEM and NAB/GEM + ACT,
respectively).

| | NAB/GEM | | NAB/GEM + ACT | | Saline | | ACT + NAB/GEM | |
|---|---|---|---|---|---|---|---|---|
| Time Days | Tumour volume (mm$^3$) | SEM | Tumour volume (mm$^3$) | SEM | Tumour volume (mm$^3$) | SEM | Tumour volume (mm$^3$) | SEM |
| 14 | 167.4 | 23.6 | 82.2 | 6.7 | 238.6 | 19.5 | 113.6 | 30.5 |
| 17 | 146.3 | 19.7 | 63.7 | 6.5 | 312.2 | 25.8 | 79.9 | 11.6 |
| 21 | 131.9 | 16.4 | 49.0 | 7.8 | 345.2 | 32.4 | 68.2 | 9.9 |
| 25 | 130.7 | 13.6 | 42.1 | 7.4 | 391.6 | 43.2 | 77.3 | 22.8 |
| 28 | 163.2 | 19.1 | 33.7 | 6.1 | 444.9 | 51.7 | 53.8 | 10.7 |
| 32 | 146.7 | 29.2 | 32.0 | 5.6 | 501.0 | 60.4 | 42.3 | 6.9 |
| 35 | 147.2 | 23.5 | 29.3 | 6.3 | 555.6 | 68.4 | 38.3 | 8.2 |
| 39 | 166.2 | 30.3 | 27.5 | 5.8 | 627.5 | 75.6 | 36.1 | 6.3 |
| 42 | 222.8 | 60.4 | 21.1 | 4.4 | 728.7 | 94.0 | 31.7 | 6.5 |
| 45 | 242.8 | 60.8 | 18.5 | 5.0 | 851.2 | 111.6 | 40.6 | 7.1 |
| 49 | 266.7 | 70.7 | 20.2 | 5.2 | 938.0 | 118.1 | 48.8 | 13.5 |

Figure 3:
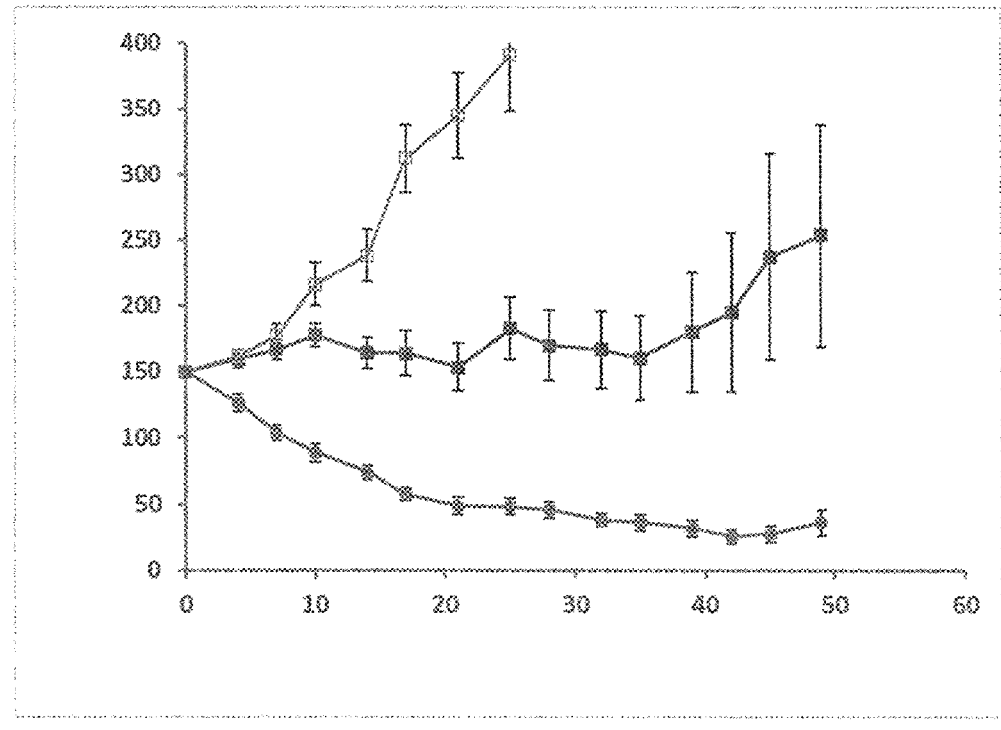
FIG. 3 provides results from the study of Example 2 wherein the Y-axis shows the tumour volume as a function of time for treatment of pancreatic ductal adenocarcinoma in mice with liposomal irinotecan (filled squares), saline control (open squares) and liposomal irinotecan in combination

The results provided in Tables 4 and 5 are visualized in FIG. 3 and FIG. 4, respectively.

FIG. 3 provides the therapeutic efficacy of ACT in combination with liposomal irinotecan for treatment of patient derived pancreatic ductal adenocarcinoma. Y-axis showing tumour volume in mm$^3$. X-axis showing time from start of study in days. Treatment was applied at days 0, 7 and 14. Treatment groups are: Saline control (open squares), liposomal irinotecan alone (filled squares) and liposomal irinotecan with ACT (filled circles).

FIG. 4 provides the therapeutic efficacy of ACT in combination with gemcitabine and nab-paclitaxel for treatment of pancreatic ductal adenocarcinoma. Y-axis showing tumour volume in mm$^3$. X-axis showing time from start of study in days. Treatment was applied at days 0, 7 and 14. Treatment groups are: Saline control (open squares), gemcitabine and nab-paclitaxel alone (filled squares), gemcitabine and nab-paclitaxel with ACT applied prior to drug administration (open circles) and gemcitabine and nab-paclitaxel with ACT applied after drug administration (filled circles).

In summary, the results show that treatment with nab-paclitaxel/gemcitabine (ABX/GEM) or liposomal irinotecan (ONI) alone showed significant inhibition of the tumour growth at the doses used. However furthermore, application of ACT according to the invention, before or after the chemotherapy treatment, dramatically enhanced the activity and therapeutic effect, and markedly induced tumour shrinkage, even >100 days after the last dose of treatment. Applying ACT following the dosing of ABX/GEM resulted in a 90% reduction in tumour volume compared to ABX/GEM alone at Day 50 after the initial drug dosing (P=0.001). Some of the mice had complete remission. At Day 120, 50% of the mice in the ABX/GEM+ACT group were still in stable, complete remission with tumour volume <50 mm$^3$ vs. 10% in the ABX/GEM alone group. Similar activity was also observed with the ONI treatment. At Day 50 after the initiation of study, ONI+ACT induced an 85% reduction in tumour volume compared to ONI alone (P=0.024). At Day 120, 60% of the mice in the ONI+ACT® treated group were still in stable, complete remission with tumour volume <50 mm$^3$ vs. 10% in the ONI alone group. Hence, there is a significant increase in the fraction of complete responders. Applying ACT right before the dosing of chemotherapeutics also showed improvement of efficacy, but slightly less than applying after the chemotherapy. Overall, these findings demonstrate the potential utility of ACT in improving the therapeutic efficacy of chemotherapeutics such as ABX/GEM and ONI treatments in PDAC and provide solid preclinical evidence that supports evaluation in patients. It also provides insights for the design of clinical trials.

Example 3. Therapeutic Effects in a Subcutaneous Mouse Models for Hepatocellular Carcinoma (HCC)—Cancer Immunotherapy with Reovirus±Acoustic Cluster Therapy The current example reports the effect of ACT in combination with an oncolytic virus for treatment of HCC. This disease model resembles PDAC in a number of vital characteristics, see J Gastrointest Oncol. 2018 February; 9(1): 180-195. doi: 10.21037/jgo.2017.06.09) and, hence, provides relevant data in support of the current invention.

Oncolytic viruses are a form of cancer immunotherapy that uses viruses to infect and destroy cancer cells. Viruses are particles that infect or enter our cells and then use the cell's genetic machinery to make copies of themselves and subsequently spread to surrounding uninfected cells. Recently, viruses have been used to target and attack tumours that have already formed. These viruses are known as oncolytic viruses and they represent a promising approach to treating cancer. Cancer cells often have impaired antiviral defenses that make them susceptible to infection. After infection, these oncolytic viruses can cause cancer cells to "burst", killing the cancer cells and releasing cancer antigens. These antigens can then stimulate immune responses that can seek out and eliminate any remaining tumour cells nearby and potentially anywhere else in the body.

Viruses from the reoviridare family (reoviruses) have been extensively explored for treatment of PDAC (NCT01280058, NCT02620423, NCT03723915) with clear evidence or therapeutic benefit. However, a factor which may reduce the efficacy of reoviruses is limited uptake by the cancer cells. In this respect, it is envisioned that combining ACT with virus therapies may strongly increase the viral uptake and hence lead to an increase in therapeutic efficacy.

Study Design: Acoustic Cluster Therapy (ACT) and compositions for use according to the invention (referred to as ACT) was investigated for therapeutic effect level in combination with an oncolytic reovirus.

The ACT procedures applied were as described in Example 2.

HCC tumour xenografts were implanted by subcutaneous injection in balb/C mice. $1 \times 10^7$ cancer cells were injected in the flank and allowed to grow freely for approximately 21 days prior to enrolment into the study. The mice (N=5 per group) were treated with either reovirus alone or in combination with ACT. In addition, a phosphate buffer saline control group was investigated. Virus was administered six times at days 0, 5, 7, 10, 14 and 16. A dose of $1 \times 107$ Plaque Forming Units (PFU) per day was administered intravenously immediately prior to ACT treatment. The animals were monitored twice a week for body weight and tumour size (volume) via caliper measurement for the duration of the study (25 days).

Results:

The results for average tumour volume and standard error of the mean (SEM) are stated in Table 6 below, and visualized in FIG. 7.

TABLE 6

Results for average tumour volume and standard error of the mean (SEM) vs. time, of treatment groups as detailed.

| Time Days | PBS control Tumour volume (mm³) | SEM | Reovirus Tumour volume (mm³) | SEM | Reovirus + ACT Tumour volume (mm³) | SEM |
|---|---|---|---|---|---|---|
| 0 | 1.9 | 0.9 | 2.2 | 0.8 | 0.5 | 0 |
| 5 | 0.6 | 0.1 | 2.2 | 0.8 | 0.5 | 0 |
| 7 | 5.1 | 4.4 | 10.1 | 6.0 | 0.5 | 0 |
| 10 | 6.4 | 3.0 | 9.9 | 3.3 | 0.5 | 0 |
| 14 | 13.7 | 12.2 | 16.3 | 11.8 | 0.5 | 0 |
| 16 | 27 | 24.8 | 13.6 | 12.2 | 0.5 | 0 |
| 17 | 27 | 14.8 | 37.2 | 18.7 | 0.5 | 0 |
| 21 | 100.7 | 67.1 | 97.2 | 31.4 | 7.9 | 6.1 |
| 25 | 178.2 | 96.8 | 152.1 | 49.0 | 31.4 | 18.3 |

FIG. 7 provides the therapeutic efficacy of ACT in combination with oncolytic reo-virus for treatment of hepatocellular carcinoma. Y-axis showing tumour volume in mm³. X-axis showing time from start of study in days. Grey triangles below x-axis designate treatment days. Treatment groups are: Saline control (inverted triangles), oncolytic reo-virus aline (filled squares) and oncolytic reo-virus with ACT (filled circles).

As can be observed from the results displayed in Table 6 and visualized in FIG. 7, treatment with reovirus alone showed no significant inhibition of tumour growth at the investigated dose when compared to the PBS control group. However, when combining the same dose of virus with ACT treatment a marked and significant tumour inhibition was observed, with a >95% reduction in tumour volume at Day 25 vs. virus alone. At Day 25, p-value was calculated using a two-tailed ANOVE test at 95% confidence interval (nonparametric Kruskal-Wallis test with Dunns multiple comparison correction) to p=0.037.

This study hence confirms a strong synergistic effect when combining an immune therapy treatment with reovirus with ACT according to the current invention. Similar synergistic effects would be expected for treatment of PDAC as the disease model used in the example resembles PDAC in a number of vital characteristics.

Example 4 (Prospective). A Pilot Study of Acoustic Cluster Therapy (ACT) with PD-1 Antibody in a Syngeneic Mouse Model for Pancreatic Cancer Introduction: Despite huge successes in many cancer types, cancer immunotherapies such as immune checkpoint inhibitors have not shown any meaningful benefit in patients with pancreatic ductal adenocarcinoma (PDAC). The 3 main factors that contribute to this ineffectiveness are 1) low tumour immunogenicity, 2) low T-cell recruitment and 3) T-cell inactivation by cytokines. The stromal desmoplasia with its high interstitial fluid pressure, physically impedes T cell infiltration and chemically caused intra-tumour hypoxia to release immunosuppressive cytokine by stromal cells, repelling T-cells activation [Hilmi et al., World J Gastroenterol 24, 2137-2151]. Acoustic Cluster Therapy (ACT) [Sontum et al., International Journal of Pharmaceutics 495 (2015) 1019-1027], a novel approach for ultrasound (US) mediated drug delivery, uses a dispersion of negatively charged microbubble and positively charged microdroplet clusters to induce enhanced local permeability of the vasculature upon local US insonation, allowing extravasation of drug into the tumour tissues. By using the ACT approach to increase vasculature permeability of PDAC, we can potentially increase T cell infiltration and increase the delivery of immunotherapeutics to improve T-cell activation. Therefore, this may lead to a major impact on the treatment outcome of immunotherapy in patients with PDAC.

Objectives: The aim of the study is to evaluate the antitumour activity of ACT in combination with a PD-1 antibody in a syngeneic mouse model for pancreatic cancer.

Experimental Design

A—Evaluation of Antitumour Activity of ACT in Combination with PD-1 Antibody in a Syngeneic Mouse Model for Pancreatic Cancer The ACT procedures applied will be as described in Example 2.

A syngeneic murine PDAC model will be used in this study. The model uses a murine PDAC cell line derived from the KPC genetically engineered mouse model which has been shown to closely recapitulate human PDAC [Hingorani et al, Cancer Cell 7, 469-483] [Lee et al., Curr Protoc Pharmacol 73, 14 39 11-14 39 20]. Cells will be inoculated subcutaneously to the flanks of C57BL/6J (BLACK 6) mice. To evaluate the efficacy of ACT based treatment, mice will be enrolled into four treatment groups: (1) Isotype IgG control, (2) Isotype IgG+ACT only, (3) PD-1 antibody, (4) PD-1 antibody+ACT, at 14 mice/group.

PD-1 antibody (0.2 mg/mouse) will be given i.p. on days 0, 3, 7 and 10. Tumours will be measured using a caliper and tumour volumes calculated using the formula: Tumour volume=(a×b2/2) where 'b' is the smallest diameter and 'a' is the largest diameter. Once the established tumours reach approximately 50-150 mm³, the mice will be pair-matched into the various treatment groups in order to reduce the variability of tumour sizes per group. On the same day, antibody and ACT will be administered according to the schedule (at total of 4 doses). When the individual tumours of each mouse reach an approximate end-point (tumour volume >1,500 mm³), the mouse is sacrificed with regulated $CO_2$. The tumour growth inhibition (TGI) will be calculated by comparing the control group's tumour measurements with the other study groups once the predetermined endpoint is reached in the control group.

US 12,622,867 B2

37

B—Evaluation of Increased Immune Cells Presence with Activity of ACT

To evaluate the changes in the tumour immune microenvironment upon the treatments, 4 mice from each group will be sacrificed one hour after the last drug dose on Day 10. Blood and tumour tissues will be harvested. Half of the tumour tissues from each mouse will be flash-frozen and the other half will be Formalin-fixed paraffin-embedded (FFPE-processed). The FFPE tissues will be analyzed using immunohistochemistry (IHC) including hematoxylin and eosin (H&E) staining and the immune markers: F4/80, CD3, CD4, CD8 and Foxp3.

Results (prospective): the results will show that, compared to anti-PD1 treatment alone, the combination with ACT leads to meeting one or more of the following therapeutic efficacy end-points; a significant increase in TGI, a significant increase in median overall survival, a significant increase in tumour infiltration of immune cells.

This study will hence confirm a strong synergistic effect when combining an immune therapy treatment with anti-PD1 with ACT according to the current invention.

Example 5 (Prospective). Manufacture of Cluster Compositions with Various Microbubble and Microdroplet Components In order to show that the invention is applicable for a variety of chemical compositions of C1 and C2, several formulations will be manufactured or sourced commercially and explored for the in-vitro attributes of the resulting cluster composition.

C1 Examples

The commercially available microbubble US imaging agents Sonovue (Bracco Spa, Italy) and Micromarker (VisualSonics Inc., USA) will be sourced and used as C1 components. Sonovue is a sulphur hexafluoride microbubble stabilized with a membrane of distearoylphosphatidylcholine, dipalmitoylphosphatidylglycerol sodium, palmitic acid and PEG4000, and presented in a lyophilized form to be reconstituted with 5 mL of aqueous matrix. Micromarker is a perfluorobutane/nitrogen microbubble stabilized with phospholipids, polyethylenglycol and fatty acid, and presented in a lyophilized form for reconstitution with 0.7 mL of aqueous matrix.

C2 Examples

Microdroplet (C2) components with diffusible components; perfluorodimethylcyclobutane, 2-(trifluoromethyl) perfluoropentane and perfluorohexane will be manufactured as follows:

790 mg distearoylphosphatidylcholine (DSPC) and 8.1 mg stearylamine (SA) will be weighed into a 250 ml round bottom flask and 50 ml chloroform will be added. The sample will be heated under hot tap water until a clear solution is obtained. The chloroform will be removed by evaporation to dryness on a rotary evaporator at 350 mm Hg and 40° C., followed by further drying at 50 mm Hg in desiccator overnight. Thereafter, 160 ml water will be added and the flask again placed on a rotary evaporator and the lipids rehydrated by full rotational speed and 800° C. water bath temperature for 25 minutes. The resulting lipid dispersion will be transferred to a suitable vial and stored in refrigerator until use.

Emulsions will be prepared by transferring aliquots of 1 ml of the cold lipid dispersion to 2 ml chromatography vials. Each of 6 vials will be added 100 µl of the fluorocarbon oils as detailed above. The chromatography vials will be shaken on a CapMix (Espe, GmbH) for 75 seconds. The resulting emulsion will be washed three times by centrifugation and removal of infranatant followed by addition of equivalent volume of an aqueous 5 mM TRIS buffer. The vials will immediately be cooled on ice, pooled and kept cold until use.

Coulter counter analysis will be performed to determine the volume concentration and diameter of the microdroplets, and the emulsions will then be diluted with 5 mM TRIS buffer to a disperse phase concentration 4 µl microdroplets/ml.

Preparation of cluster compositions is to be performed by reconstituting Sonovue or Micromarker with 5 or 0.7 mL, respectively, of each of the C2 components described above. Results (Prospective).

Upon mixing of components C1 and C2, all six combinations are expected to contain more than 10 million clusters per ml, with a mean diameter between 3 to 10 µm.

The invention claimed is:

1. A method of Acoustic Cluster Therapy (ACT) treatment comprising:
(i) administering a pharmaceutical composition to a mammalian subject with pancreatic cancer; wherein the pharmaceutical composition comprises:
(a) a cluster composition which comprises a suspension of clusters in an aqueous biocompatible medium, where said clusters have a mean diameter in the range 3 to 10 µm, and a circularity <0.9, and wherein the cluster concentration of clusters in the size range 3-10 µm is at least 10 million/ml, the cluster composition comprises:
(i) a first component which comprises gas microbubbles and first stabilizer to stabilize said microbubbles; and
(ii) a second component which comprises microdroplets comprising an oil phase and second stabilizer to stabilize said microdroplets, where the oil phase comprises a diffusible component capable of diffusing into said gas microbubbles so as to at least transiently increase the size thereof, wherein the microbubbles and microdroplets of said first and second components have opposite surface charges and form said clusters via attractive electrostatic interactions; and
(b) a therapeutic agent selected from the group consisting of chemotherapeutic agents, immunotherapeutic agents, and combinations thereof, wherein when the therapeutic agent includes said chemotherapeutic agents, and wherein when said chemotherapeutic agents include paclitaxel, said paclitaxel is in an albumin-bound form, wherein the at least one therapeutic agent is pre-, and/or co-and/or post administered separate to the cluster composition;
(ii) optionally imaging the clusters of said pharmaceutical composition using ultrasound imaging to identify a region of interest for treatment within said subject;
(iii) activating a phase shift of the diffusible component of the second component of the cluster composition from step (i) by ultrasound insonation of a region of interest within said subject; and (iv) facilitating extravasation of the therapeutic agents administered in step (i) by further ultrasound irradiation.

2. The method of claim 1, wherein the step (iii) of activating the phase shift is performed with ultrasound insonation at a frequency of 1 to 10 MHz and with a mechanical index of 0.1 to 0.7.

3. The method of claim 1, wherein the step (iv) facilitating extravasation is performed with ultrasound insonation at a frequency of 330 to 650 kHz and with a mechanical index of 0.15 to 0.4.

4. The method of claim 1, wherein the steps (i) to (iv) of the ACT treatment are repeated one to four times.

5. The method of claim 1, wherein the insonation of step (iii) activating the phase shift starts immediately after step (i) and is immediately followed by the insonation of step (iv) facilitating extravasation.

6. The method of claim 1, wherein the insonation of step (iii) lasts for 30-120 seconds, followed by the insonation of step (iv) which lasts for 3-10 minutes.

7. The method of claim 1, wherein 1 to 5 therapeutic agents are administered simultaneously or sequentially over a certain time span wherein at least one ACT treatment is performed during the same period.

8. The method of claim 1, wherein a broad band or dual frequency ultrasound transducer is used in both the activating insonation of step (iii) and the further ultrasound of step (iv).

9. A method of delivering a therapeutic agent, wherein the method comprises the steps of:

(i) administering a pharmaceutical composition to a subject with pancreatic ductal adenocarcinoma (PDAC); wherein the pharmaceutical composition comprises:

(a) a cluster composition which comprises a suspension of clusters in an aqueous biocompatible medium, where said clusters have a mean diameter in the range 3 to 10 μm, and a circularity <0.9, and wherein the cluster concentration of clusters in the size range 3-10 μm is at least 10 million/ml, the cluster composition comprises:

(i) a first component which comprises gas microbubbles and first stabilizer to stabilize said microbubbles; and (ii) a second component which comprises microdroplets comprising an oil phase and second stabilizer to stabilize said microdroplets, where the oil phase comprises a diffusible component capable of diffusing into said gas microbubbles so as to at least transiently increase the size thereof, wherein the microbubbles and microdroplets of said first and second components have opposite surface charges and form said clusters via attractive electrostatic interactions; and (b) a therapeutic agent selected from the group consisting of chemotherapeutic agents, immunotherapeutic agents, and combinations thereof, wherein when the therapeutic agent includes said chemotherapeutic agents, and wherein when said chemotherapeutic agents include paclitaxel, said paclitaxel is in an albumin-bound form, wherein the least one therapeutic agent is pre-, and/or co-and/or post administered separate to the cluster composition, and before steps ii) to iii) or after any of steps ii) to iii);

(ii) optionally imaging the clusters of said pharmaceutical composition using ultrasound imaging to identify a region of interest for treatment within said subject;

(iii) activating a phase shift of the diffusible component of the second component of the cluster composition from step (i) by ultrasound irradiation of a region of interest within said subject, such that:

(a) the microbubbles of said clusters are enlarged by said diffusible component of step (iii) to give enlarged bubbles which are localised at said region of interest due to temporary blocking of the microcirculation at said region of interest by said enlarged bubbles; and (b) facilitating extravasation of the therapeutic agent(s) administered in step (i); and (iv) facilitating further extravasation of the therapeutic agents administered in step (i) by further ultrasound irradiation.

* * * * *